United States Patent
Poitzsch et al.

(10) Patent No.: US 6,246,236 B1
(45) Date of Patent: Jun. 12, 2001

(54) APPARATUS AND METHOD FOR OBTAINING A NUCLEAR MAGNETIC RESONANCE MEASUREMENT WHILE DRILLING

(75) Inventors: Martin E. Poitzsch; Steven F. Crary; Krishnamurthy Ganesan, all of Sugar Land; Ralf Heidler, Stafford; Bruno Luong, Stafford; Peter Speier, Stafford, all of TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/186,950

(22) Filed: Nov. 5, 1998

Related U.S. Application Data

(63) Continuation-in-part of application No. 09/033,965, filed on Mar. 3, 1998.

(51) Int. Cl.[7] .................................................. G01V 3/00
(52) U.S. Cl. .................................................. 324/303
(58) Field of Search ................................. 324/303, 300, 324/312, 314, 318, 307, 309, 322

(56) References Cited

U.S. PATENT DOCUMENTS

| | | |
|---|---|---|
| 4,717,878 | 1/1988 | Taicher et al. . |
| 4,949,045 | 8/1990 | Clark et al. . |
| 5,023,551 | 6/1991 | Kleinberg et al. . |
| 5,055,787 | 10/1991 | Kleinberg et al. . |
| 5,212,447 | 5/1993 | Paltiel . |
| 5,280,243 | 1/1994 | Miller . |
| 5,363,041 | 11/1994 | Sezginer . |
| 5,381,092 | 1/1995 | Freedman . |
| 5,432,446 | 7/1995 | MacInnis et al. . |
| 5,471,140 | 11/1995 | Hanley . |
| 5,557,201 | 9/1996 | Kleinberg et al. . |
| 5,596,274 | 1/1997 | Sezginer . |
| 5,705,927 | 1/1998 | Sezginer et al. . |
| 5,757,186 | 5/1998 | Taicher et al. . |
| 5,796,252 | 8/1998 | Kleinberg et al. . |
| 5,828,214 | * 11/1998 | Taicher et al. ................ 324/303 |
| 6,049,205 | * 4/2000 | Taicher et al. ................ 324/303 |

FOREIGN PATENT DOCUMENTS

| | | |
|---|---|---|
| 0 237 323 A2 | 9/1987 | (EP) . |
| 2 310 500 | 8/1997 | (GB) . |
| 2 311 864 | 10/1997 | (GB) . |
| WO 98/29639 | 7/1998 | (WO) . |

OTHER PUBLICATIONS

R. S. Dembo and U. Tulowitzki, "On the Minimization of Quadratic Functions Subject to Box Constraints," Yale Univ. School of Organization and Management, SOM Working Paper Series B #71, New Haven(1983).

* cited by examiner

Primary Examiner—Louis Arana
(74) Attorney, Agent, or Firm—John J. Pyberg; Brigette L. Jeffery

(57) ABSTRACT

The present invention is directed to a nuclear magnetic resonance logging-while-drilling tool. The tool comprises a drill bit, drill string, a plurality of RF antennas, and at least one gradient coil. The tool further comprises a plurality of magnets that are polarized in a direction parallel to the longitudinal axis of the tool but opposite to each other. The configuration of magnets and antennas provides for at least two NMR regions of investigation.

52 Claims, 12 Drawing Sheets

APPARATUS AND METHOD FOR OBTAINING A NUCLEAR MAGNETIC RESONANCE MEASUREMENT WHILE DRILLING

CROSS-REFERENCES

This is a continuation-in-part of U.S. patent application Ser. No. 09/033,965; filed Mar. 3, 1998.

BACKGROUND OF THE INVENTION

The present invention relates generally to an apparatus and method for measuring nuclear magnetic resonance properties of an earth formation traversed by a borehole, and more particularly, to an apparatus for obtaining a nuclear magnetic resonance measurement while drilling the borehole.

It is well recognized that atomic particles of an earth formation having non-zero nuclear spin magnetic moment, for example protons, have a tendency to align with a static magnetic field imposed on the formation. Such a magnetic field may be naturally generated, as is the case for the earth's magnetic field, $B_E$. An RF pulse applying a second magnetic field transverse to $B_E$ creates a magnetization component in the transverse plane (perpendicular to $B_E$) which precesses about the $B_E$ vector with a characteristic resonance known as the Larmor frequency, $\omega_L$, which depends on the strength of the static magnetic field and the gyromagnetic ratio of the particle. Hydrogen nuclei (protons) precessing about a magnetic field $B_E$ of 0.5 gauss, for example, have a characteristic frequency of approximately 2 kHz. If a population of hydrogen nuclei were made to precess in phase, the combined magnetic fields of the protons can generate a detectable oscillating voltage in a receiver coil, conditions known to those skilled in the art as free induction decay or a spin echo. Hydrogen nuclei of water and hydrocarbons occurring in rock pores produce nuclear magnetic resonance (NMR) signals distinct from signals arising from other solids.

U.S. Pat. No. 4,717,878 issued to Taicher et al. and U.S. Pat. No. 5,055,787 issued to Kleinberg et al., describe NMR tools which employ permanent magnets to polarize hydrogen nuclei and generate a static magnetic field, $B_0$, and RF antennas to excite and detect nuclear magnetic resonance to determine porosity, free fluid ratio, and permeability of a formation. The atomic nuclei align with the applied field, $B_0$, with a time constant of $T_1$. After a period of polarization, the angle between the nuclear magnetization and the applied field can be changed by applying an RF field, $B_1$, perpendicular to the static field $B_0$, at the Larmor frequency $f_L = \gamma B_0/2\pi$, where $\gamma$ is the gyromagnetic ratio of the proton and $B_0$ designates the static magnetic field strength. After termination of the RF pulse, the protons precess in the plane perpendicular to $B_0$. A sequence of refocusing RF pulses generates a sequence of spin-echoes which produce a detectable NMR signal in the antenna.

U.S. Pat. No. 5,280,243 issued to Melvin Miller describes a nuclear magnetic resonance tool for formation evaluation while drilling. The tool includes a probe section consisting of a permanent magnet disposed in a longitudinally extending annular recess outside the drill collar and an antenna disposed on a non-conductive magnetic sleeve outside the drill collar. The gradient of the static magnetic field magnitude is in the radial direction. The antenna produces an RF magnetic field substantially perpendicular to both the longitudinal axis of the tool and the static field direction. With the '243 apparatus, the magnet must be long in axial extent compared to its diameter for the magnetic fields to approximate its intended 2-D dipole behavior.

U.S. Pat. No. 5,757,186 issued to Taicher et al. describes a measurement-while-drilling tool which includes a sensing apparatus for making nuclear magnetic resonance measurements of the earth formation. The NMR sensing apparatus is mounted in an annular recess formed into the exterior surface of the drill collar. In one embodiment, a flux closure is inserted into the recess. A magnet is disposed on the outer radial surface of the flux closure. The magnet is constructed from a plurality of radial segments which are magnetized radially outward from the longitudinal axis of the tool. The flux closure is required to provide suitable directional orientation of the magnetic field.

The tools disclosed in the '243 and '186 patents suffer from common problems: both tools require using a nonconductive magnet and placing the magnet outside the drill collar. For the '243 tool, the outside surface of the drill collar must contain a recessed area to accommodate the nonconductive magnet. For the '186 tool, the outside surface of the drill collar must contain a recessed area to accommodate the flux closure, nonconductive magnet, and antenna. Because the strength of the drill collar is a function of its radii, reducing the external diameter to accommodate the magnet only or the flux closure, magnet, and antenna results in an unacceptably weak section of the drill collar which may bend or break during the drilling operation.

U.S. Pat. No. 5,557,201 issued to Kleinberg et al. describes a pulsed nuclear magnetism tool for formation evaluation while drilling. The tool includes a drill bit, drill string, and a pulsed nuclear magnetic resonance device housed within a drill collar made of nonmagnetic alloy. The tool includes a channel, within the drill string and pulsed NMR device, through which drilling mud is pumped into the borehole. The pulsed NMR device comprises two tubular magnets, which are mounted with like poles facing each other, surrounding the channel, and an antenna coil mounted in an exterior surface of the drill string between the magnets. This tool is designed to resonate nuclei at a measurement region known to those skilled in the art as the saddle point.

U.S. Pat. No. 5,705,927 issued to Sezginer et al. also describes a pulsed nuclear magnetism tool for formation evaluation while drilling. The tool includes shimming magnets, located either inside or outside the tool, which suppress the magnetic resonance signal of the borehole fluids by raising the magnitude of the static magnetic field in the borehole so that the Larmor frequency in the borehole is above the frequency of the oscillating field produced by an RF antenna located in a recessed area of the tool. The shimming magnets also reduce the gradient of the static magnetic field in the region of investigation.

SUMMARY OF THE INVENTION

The above disadvantages of the prior art are overcome by means of the subject invention for an apparatus and method for obtaining a nuclear magnetic resonance measurement while drilling the borehole. The apparatus comprises a drilling means for drilling a borehole into the formation, a means for carrying drilling fluid through the drilling means, and a measuring means for making nuclear magnetic resonance measurements the borehole is being drilled. The measuring means produces a plurality of substantially axisymmetric static magnetic fields through the drilling means and into the formation at a plurality of regions of investigation. The measuring means also generates an oscillating magnetic field in the formation. At least one magnetically permeable member is located inside the drilling means for shaping the static magnetic field so that the contour lines generated by at least one static magnetic field are substantially straight in the axial direction. The apparatus further comprises a gradient means for applying a magnetic field gradient to completely dephase or incompletely dephase spins in a portion of the investigation regions.

The plurality of substantially axisymmetric static magnetic fields may include the following combinations: a low gradient-low gradient, high gradient-high gradient, high gradient-low gradient, low gradient-high gradient, or a combination of high gradient, low gradient, and saddle point regions. The apparatus has a plurality of antennas; each antenna generates an oscillating magnetic field in a different region of investigation.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

Figure 1:
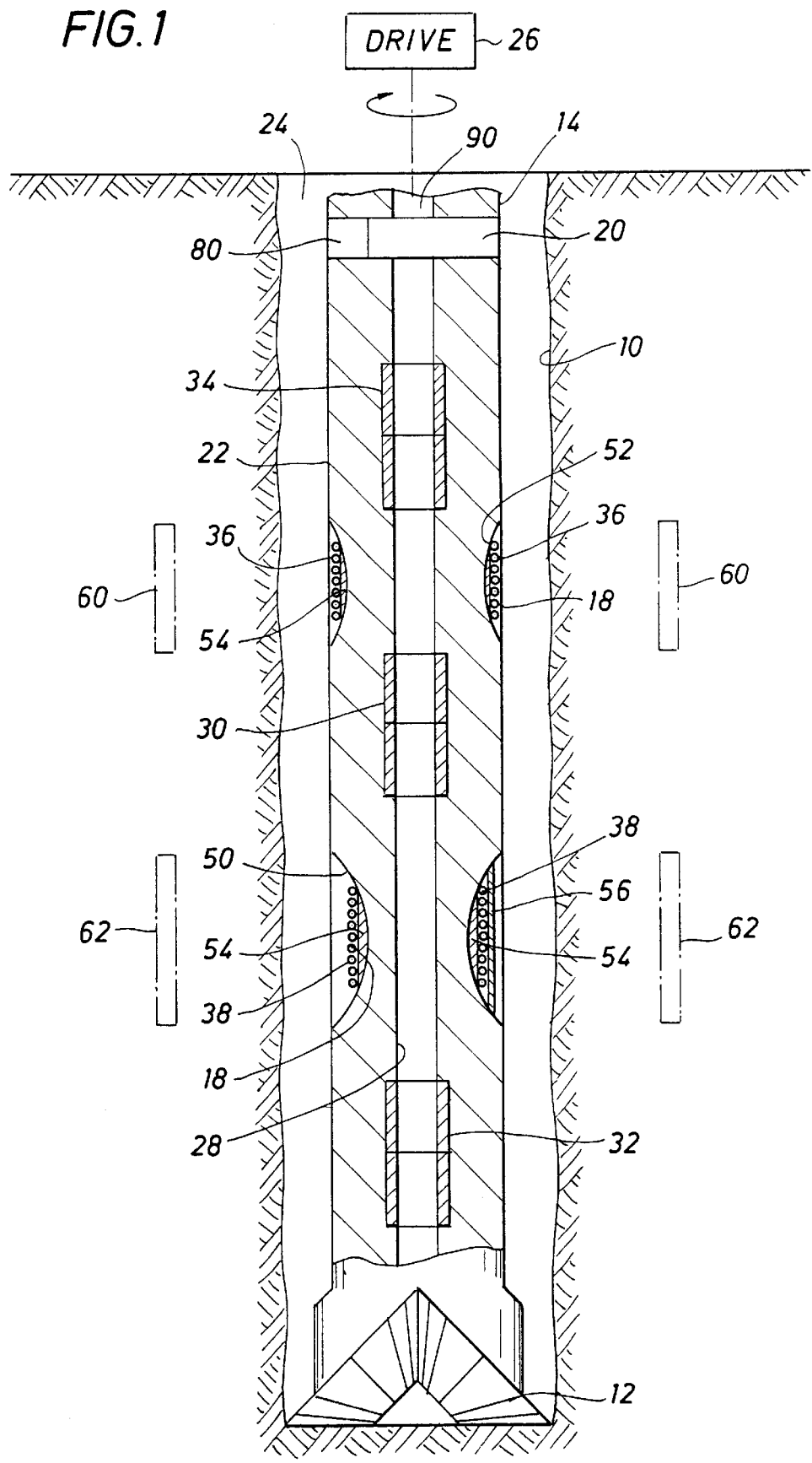
FIG. 1 illustrates a logging-while-drilling apparatus.

Referring to FIG. 1, a nuclear magnetic resonance (NMR) logging-while-drilling tool 10 is illustrated. The tool 10 comprises a drill bit 12, drill string 14, a plurality of RF antennas 36, 38, and at least one gradient coil 56. The tool 10 further comprises electronic circuitry 20 housed within the drill collar 22. The electronic circuitry 20 comprises RF resonance circuitry for the antennas 36, 38, a microprocessor, a digital signal processor, and a low voltage bus. The tool 10 further comprises a plurality of tubular magnets 30, 32, and 34 which are polarized in a direction parallel to the longitudinal axis of the tool 10 but opposite to each other, i.e., with like magnetic poles facing each other. The magnets 30, 32, and 34 comprise either a conductive or nonconductive material. The configuration of magnets 30, 32, and 34 and antennas 36, 38 provides for at least two NMR regions of investigation 60, 62 with a substantially axisymmetric static and RF magnetic field.

A means for drilling a borehole 24 in the formation comprises drill bit 12 and drill collar 22. The drill collar 22 may include a stabilizing means (not shown) for stabilizing radial motion of the tool 10 in the borehole during drilling, however, the stabilizing means is not required; therefore, the tool 10 may operate unstabilized or stabilized. Mud flow sleeve 28 defines a channel 90 for carrying the drilling fluid through the drill string 14. A drive mechanism 26 rotates the drill bit 12 and drill string 14. This drive mechanism is adequately described in U.S. Pat. No. 4,949,045 issued to Clark et al. However, a downhole mud motor may be placed in the drill string as the drive mechanism 26.

It is within contemplation of the subject invention to combine N+1 magnets to obtain at least N regions of investigation in the formation. The combinations contemplated by this invention include, but are not limited to, a low gradient-low gradient, high gradient-high gradient, high gradient-low gradient, low gradient-high gradient, or a combination of high gradient, low gradient, and saddle point regions. The combination of high and low gradient static field regions in the formation offers several advantages. For example, the high gradient region may have a higher signal-to-noise ratio but may experience signal loss when the tool 10 undergoes lateral motion in the borehole. On the other hand, the low gradient region has lower susceptibility to signal loss problems when the tool 10 is in motion. Also, with moderate tool motion, longer echo trains can be acquired in the low gradient region than in the high gradient region thereby providing more information about permeability, bound and free fluid, and hydrocarbon types. Moreover, the combination of data acquired with both gradient regions may provide quantitative information about the amount of lateral motion the tool 10 experiences and can be used to motion correct the NMR data, or, at least, quality control the data. Measurements of devices, such as strain gauges, accelerometers, or magnetometers, or any combinations of these devices, may be integrated with NMR information to quality control the data or make corrections to the spin-echo train. With the combination of high and low gradient static magnetic fields, the high gradient region exhibits more diffusion effect and therefore is of greater interest for hydrocarbon typing techniques than the low gradient region. Finally, the low gradient region has a static magnetic field having a low amplitude and therefore, this region with its lower Larmor frequency is less affected by formation and borehole fluid conductivity.

Low Gradient Sonde

Figure 2:
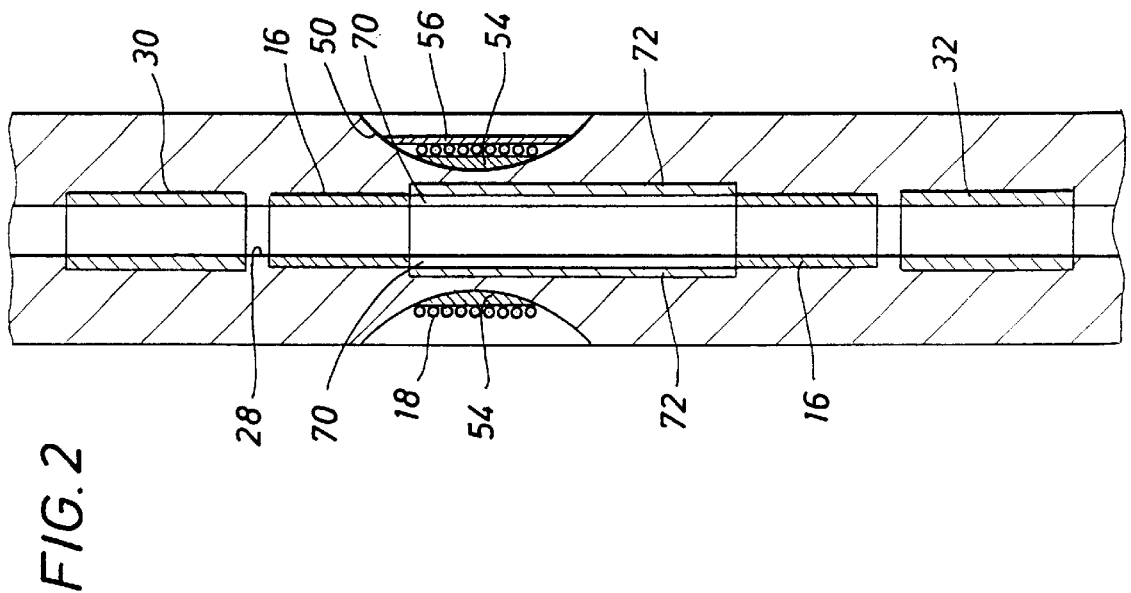
FIG. 2 depicts the low gradient sonde.
Figure 2A:
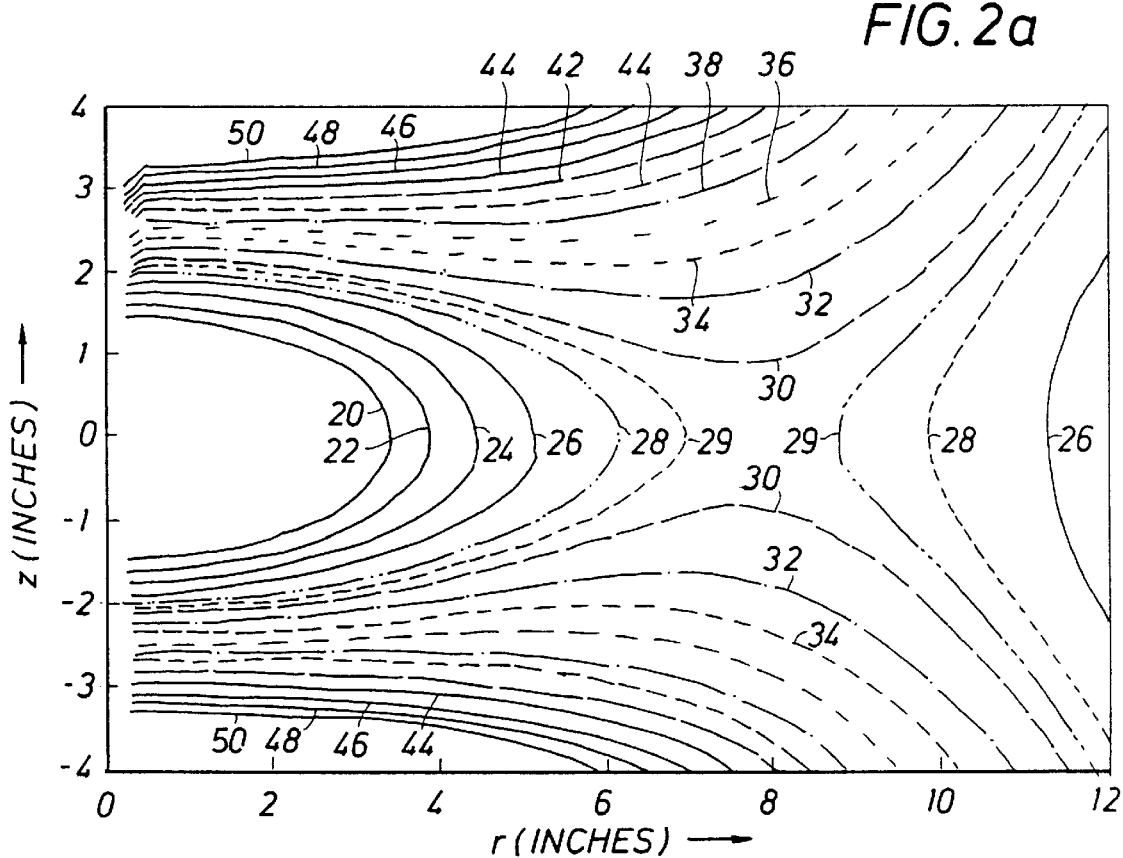
FIGS. 2a–2d illustrate the contour lines $|\vec{B}_0|$ corresponding to four low gradient magnet configurations.
Figure 2B:
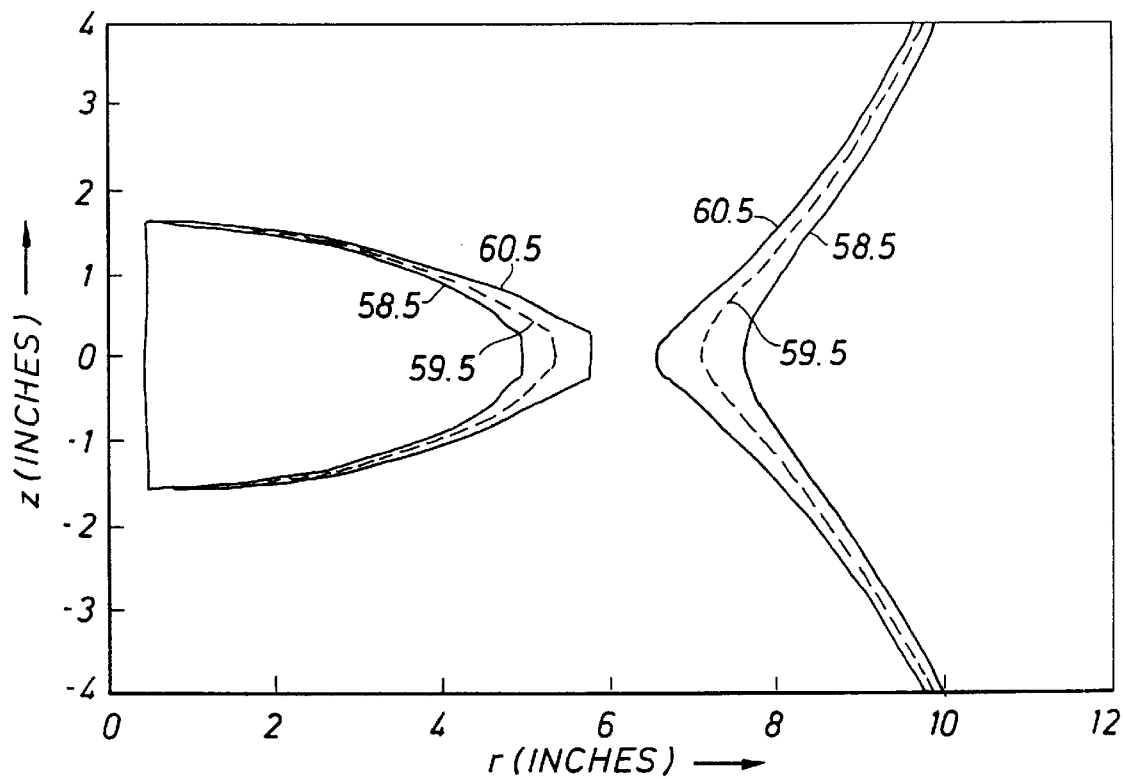

Referring to FIG. 2, in one section of the tool, hereinafter referred to as the low gradient sonde, a central magnet 30 is axially separated from a lower magnet 32. These magnets 30, 32 generate a substantially axisymmetric static magnetic field that is radial in its polarization and, over a reasonably long cylindrical shell, the static magnetic field has a fairly constant magnitude. It is within contemplation of the subject invention to excite a plurality of cylindrical shells of spins in the formation where each shell is resonant at a different RF frequency, and to sequentially interrogate each shell with sequences of RF pulses.

The area between magnets 30, 32 is suitable for housing elements such as electronic components, an RF antenna, and other similar items. For example, a plurality of electronic pockets 70 may form an integral part of the mud sleeve 28. These pockets 70 may house the RF circuitry (e.g., Q-switch, duplexer, and pre-amplifier), preferably in close proximity of the RF antenna. In a preferred embodiment of the invention, the pockets 70 form an integral part of magnetically permeable member 16. In that case, to maintain the axial symmetry of the magnetic field, a highly magnetically permeable cover 72 is located over each pocket 70.

The magnetically permeable member 16 is positioned inside the drill collar 22 between the magnets 30, 32.

Member 16 may consist of a single piece or a plurality of sections combined between the magnets 30, 32. Member 16 is constructed of a suitable magnetically permeable material, such as ferrite, permeable steel or another alloy of iron and nickel, corrosion resistant permeable steel, or permeable steel having a structural role in the member design, such as 15-5 Ph stainless steel. The magnetically permeable member 16 focuses the magnetic field and may also either carry drilling fluid through the drill string or provide structural support to the drill collar. Further, member 16 improves the shape of the static magnetic field generated by magnets 30, 32 and minimizes variations of the static magnetic field due to vertical and lateral tool motion during the period of acquiring the NMR signal. The segment of sleeve 28 between magnets 30, 32 may comprise magnetically permeable member 16. In that case, the segments of sleeve 28 under magnets 30, 32 shall consist of a non-magnetic member. Alternatively, a magnetically permeable chassis surrounding the segment of sleeve 28 between magnets 30, 32 defines member 16. In this case, the segment may consist of a magnetic or non-magnetic material. It is within contemplation of this invention to integrate the chassis and segment to form member 16.

The magnets 30, 32 are polarized in a direction parallel to the longitudinal axis of the tool 10 with like magnetic poles facing each other. For each magnet 30, 32, the magnetic lines of induction travel outward from an end of the magnet 30, 32 into the formation, along the axis of the tool 10, and travel inward to the other end of the magnet 30, 32. In the region between central magnet 30 and lower magnet 32, the magnetic lines of induction travel from the center outward into the formation, creating a static field in a direction substantially perpendicular to the axis of the tool 10. The magnetic lines of induction then travel inward symmetrically above the central magnet 30 and below the lower magnet 32 and converge in the longitudinal direction inside sleeve 28. Because of the separation, the magnitude of the static magnetic field in the central region between the central 30 and lower 32 magnet is spatially homogeneous in comparison to a saddle-point field.

The amount of separation between the magnets 30, 32 is determined based on several factors: (1) selecting the requisite magnetic field strength and homogeneity characteristics; (2) generating a field having small radial variations in the region of interest so that the echoes received during a pulse sequence (i.e., CPMG, CPI, or other sequences) are less sensitive to lateral tool motion; (3) depth of investigation; and (4) minimizing interference between the resonance circuitry and the low voltage telemetry bus in order to improve isolation of the receiving antenna which detects NMR signals from the formation. As the separation between the magnets 30, 32 decreases, the magnetic field becomes stronger and less homogeneous. Conversely, as the separation between the magnets 30, 32 increases, the magnetic field becomes weaker and more homogenous.

FIGS. 2a–2d illustrate the contour lines of $|\vec{B}_0|$ corresponding to four laboratory modeled configurations of central 30 and lower 32 magnets. These modeled results were computed using a tool having a preselected diameter (a constant diameter was used for modeling all configurations). The configuration corresponding to FIG. 2a comprises a non-magnetically permeable member separating a central 30 and lower 32 magnet by 25 inches. The configuration corresponding to FIG. 2b comprises a non-magnetically permeable member separating a central 30 and lower 32 magnet by 18 inches. The configuration corresponding to FIG. 2c comprises a non-magnetically permeable member separating a central 30 and lower 32 magnet by eight inches. The low gradient sonde, corresponding to FIG. 2d, comprises a magnetically permeable member 16 separating a central 30 and lower 32 magnet by 25 inches. The aforementioned dimensions were modeled to merely illustrate the affect of distance and/or a magnetically or non-magnetically permeable member on $|\vec{B}_0|$. FIGS. 3a–3d represent the contour lines of the gradient $|\Delta B_0|$ corresponding respectively to configurations illustrated in FIGS. 2a–2d.

Figure 3A:
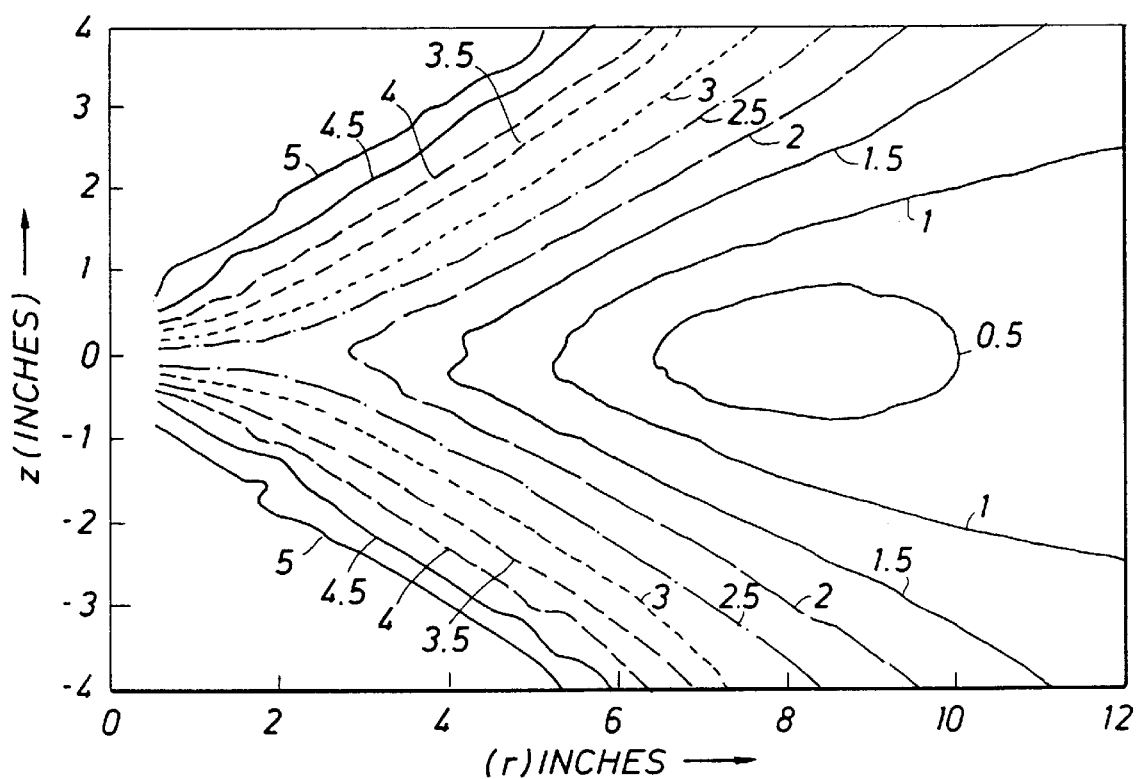
FIGS. 3a–3d represent the contour lines of the gradient $|\Delta B_0|$ corresponding to four low gradient magnet configurations.
Figure 3B:
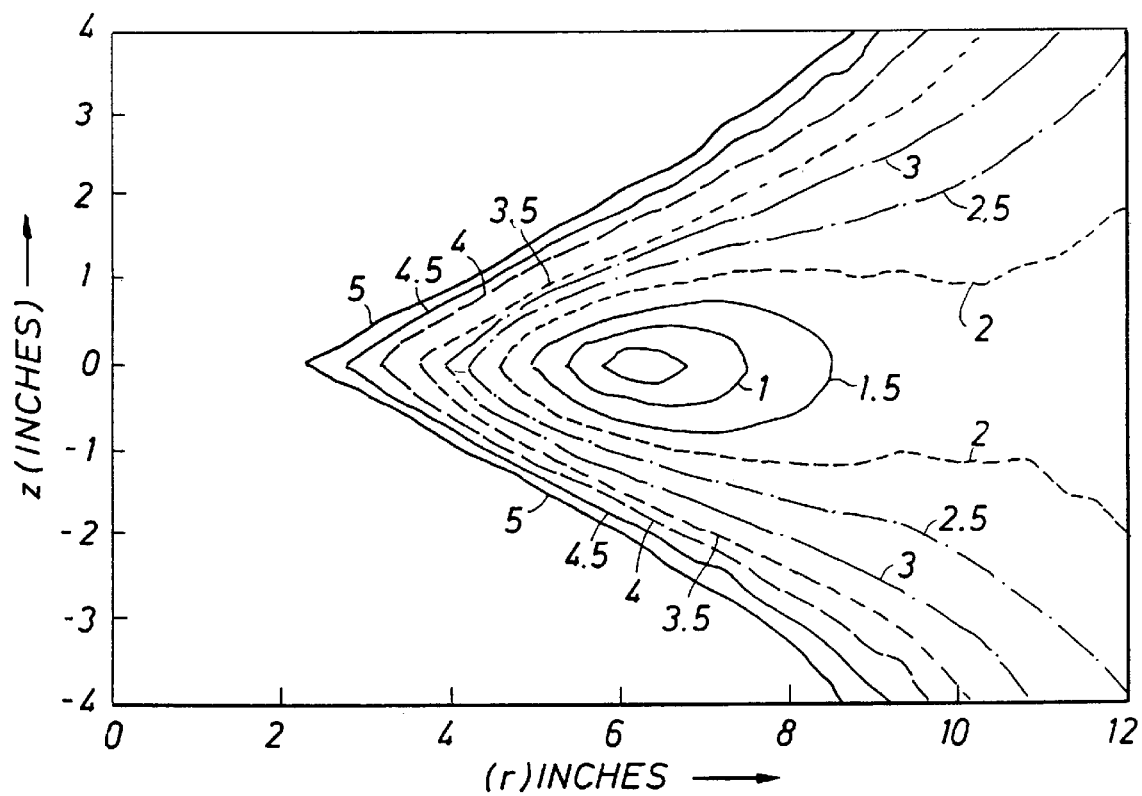
Figure 3C:
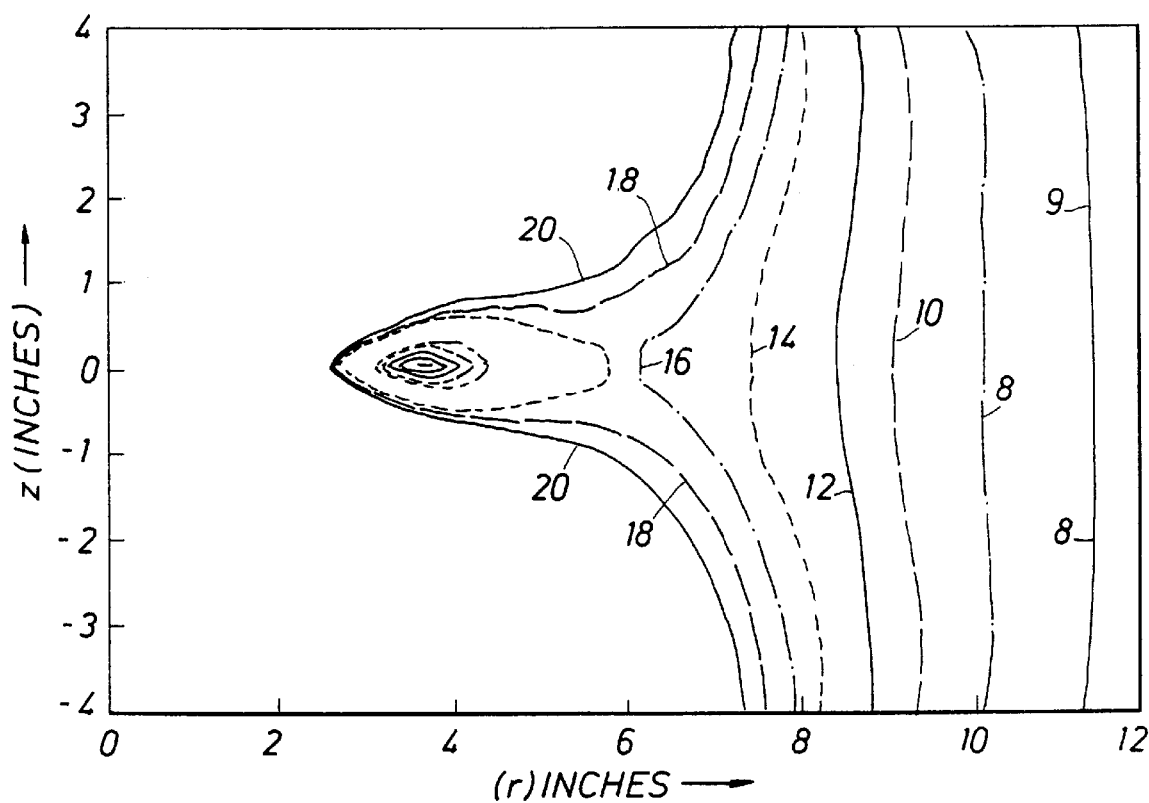
Figure 3D:
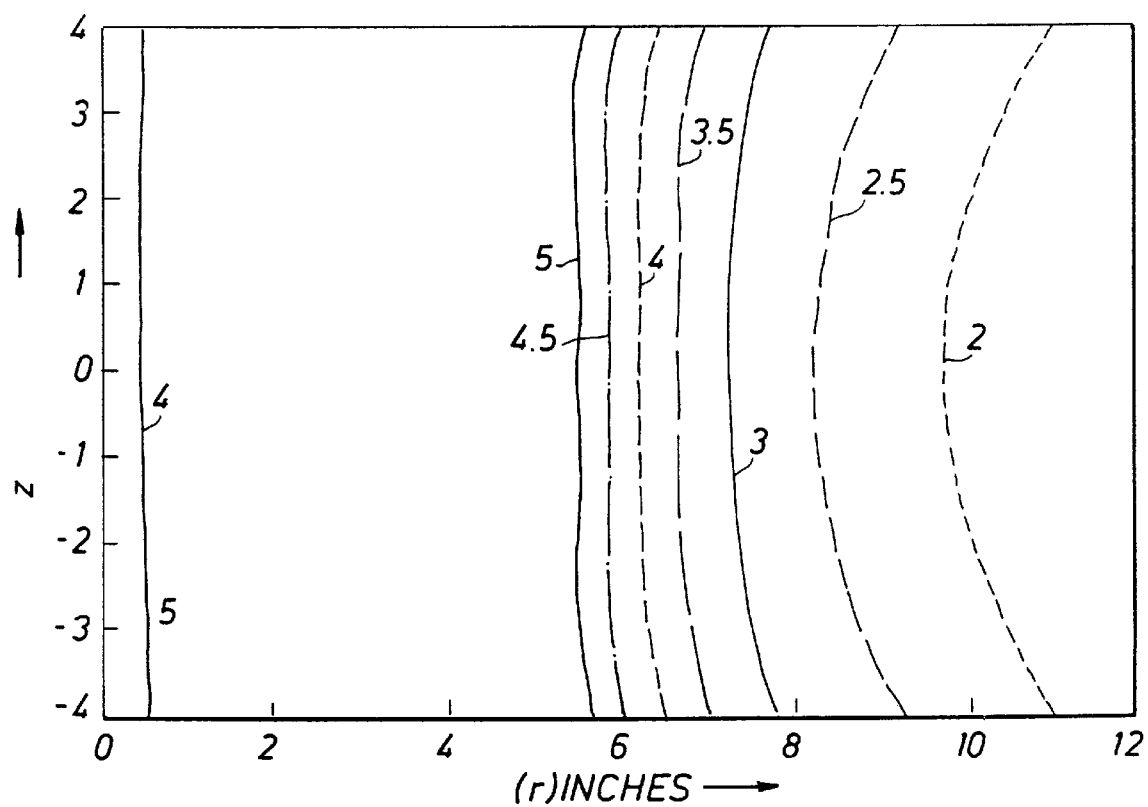

In the low gradient sonde, the magnetically permeable member 16 shunts a significant portion of the magnetic flux into the center of the tool 10. To illustrate, the magnitude of the B0 field shown in FIG. 2d at a distance of approximately seven inches radially from the longitudinal axis of tool 10 is twice as large as the $B_0$ field shown in FIG. 2a which was generated by the same magnet configuration separated by a non-magnetically permeable member. Furthermore, the low gradient sonde produces a longer and more uniform extent of the static magnetic field in the axial direction. The NMR signal measured in this section of the tool is substantially less sensitive to the vertical motion of the tool. Referring to FIG. 3d, with the low gradient sonde, a relatively small, approximately 3 Gauss/cm, gradient is measured at a distance of approximately seven inches radially from the longitudinal axis of tool. This low gradient results in a measured NMR signal which is substantially less sensitive to the lateral motion of the tool 10. When motion is moderate, longer echo trains may be acquired in this region thereby providing more information about permeability, bound and free fluid, and hydrocarbon types. In the case of the low gradient sonde, as with other gradient designs, the proton rich borehole region surrounding the tool 10 will resonate only at frequencies higher than those being applied to the volume of investigation, i.e., there is no proton borehole signal. Other NMR sensitive nuclei found in drilling mud, such as sodium-23, resonate at significantly higher static magnetic field strengths than hydrogen when excited at the same RF frequency. For the low gradient sonde, these higher field strengths are not produced in the borehole region surrounding the tool or near the antenna where such unwanted signals could be detected.

High Gradient Sonde

Figure 4:
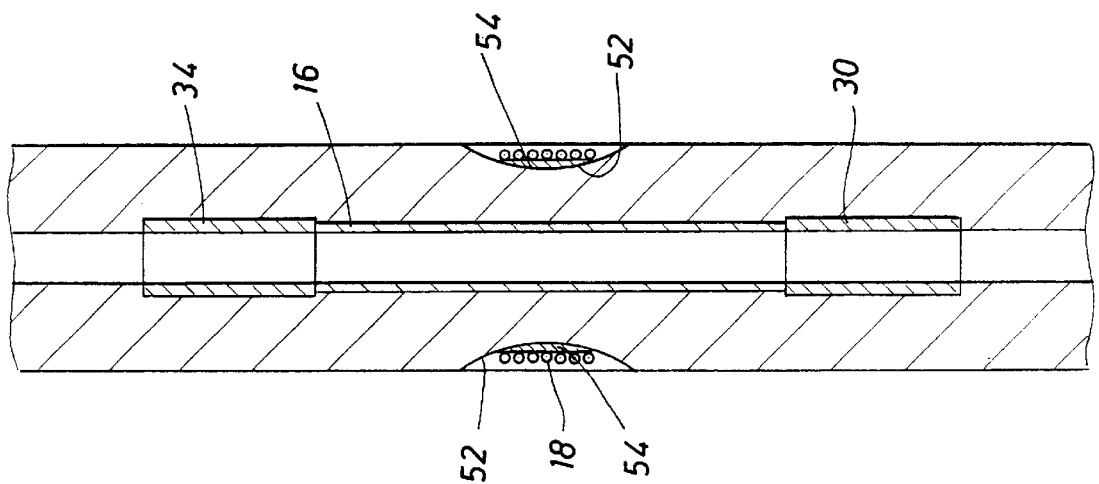
FIG. 4 depicts the high gradient sonde.

Referring to FIG. 4, in another section of the tool, hereinafter referred to as the high gradient sonde, a central magnet 30 is axially separated from an upper magnet 34. The magnets 30, 34 are polarized in a direction parallel to the longitudinal axis of the tool 10 with like magnetic poles facing each other. These magnets 30, 34 generate a substantially axisymmetric static magnetic field that is radial in its polarization and, over a reasonably long cylindrical shell, the static magnetic field has a fairly constant magnitude. It is within contemplation of the subject invention to excite a plurality of cylindrical shells of spins in the formation where each shell is resonant at a different RF frequency.

Figure 2C:
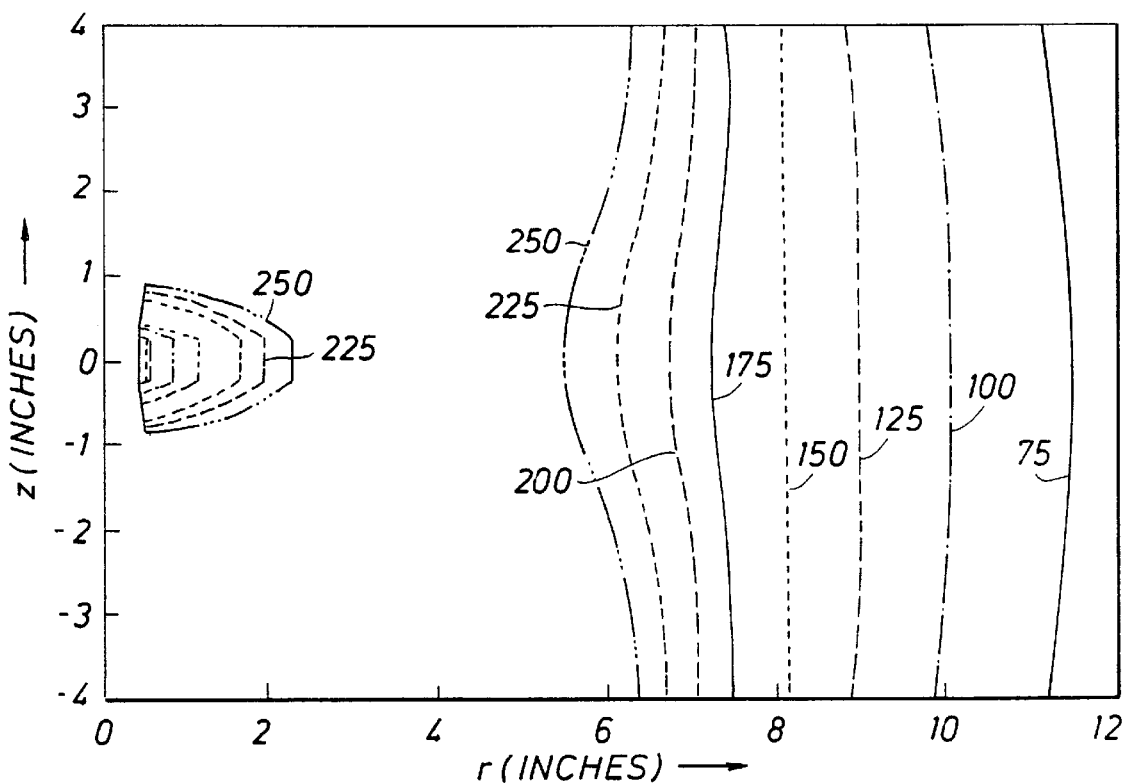
Figure 2D:
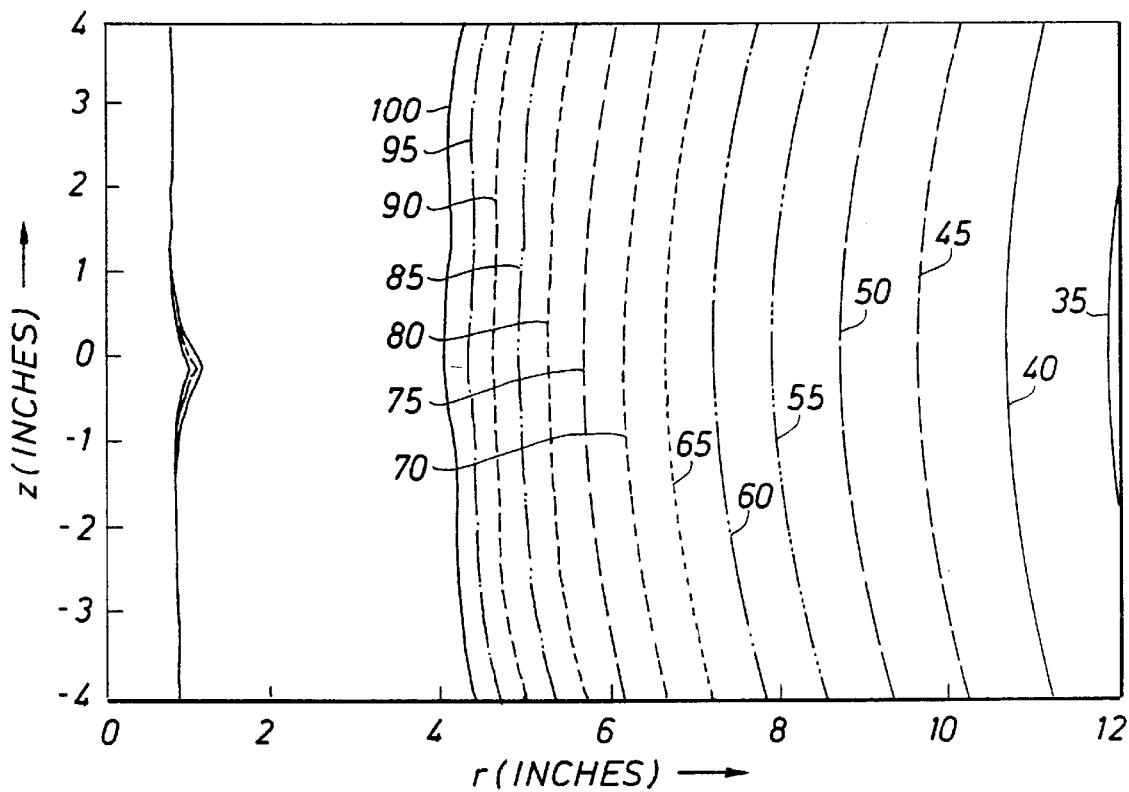

As illustrated in FIG. 2c, if the magnet separation between 30 and 34 is approximately eight inches, the contour lines of the static magnetic field strength are substantially straight and the strength of $|\vec{B}_0|$ is greater than the static magnetic field strength of the low gradient region. However, the gradient $|\Delta B_0|$ becomes larger, as illustrated in FIG. 3c, at a distance of approximately seven inches radially from the longitudinal axis of the tool. The contour lines of $|\Delta B_0|$ are curved denoting variation of the gradient in the axial direction.

Figure 4A:
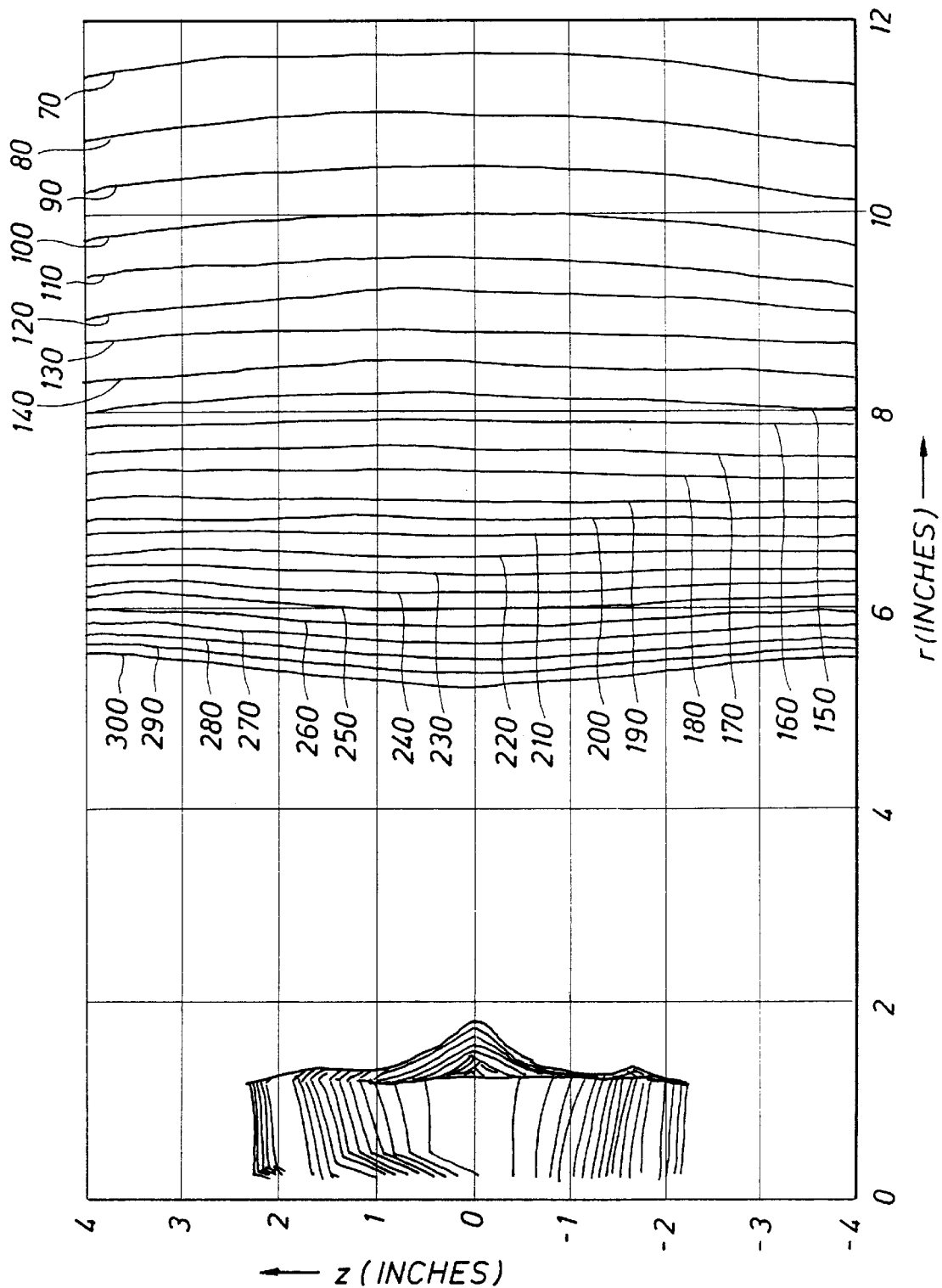
FIG. 4a represents the contour lines $|\vec{B}_0|$ corresponding to the high gradient magnet configuration.
Figure 4B:
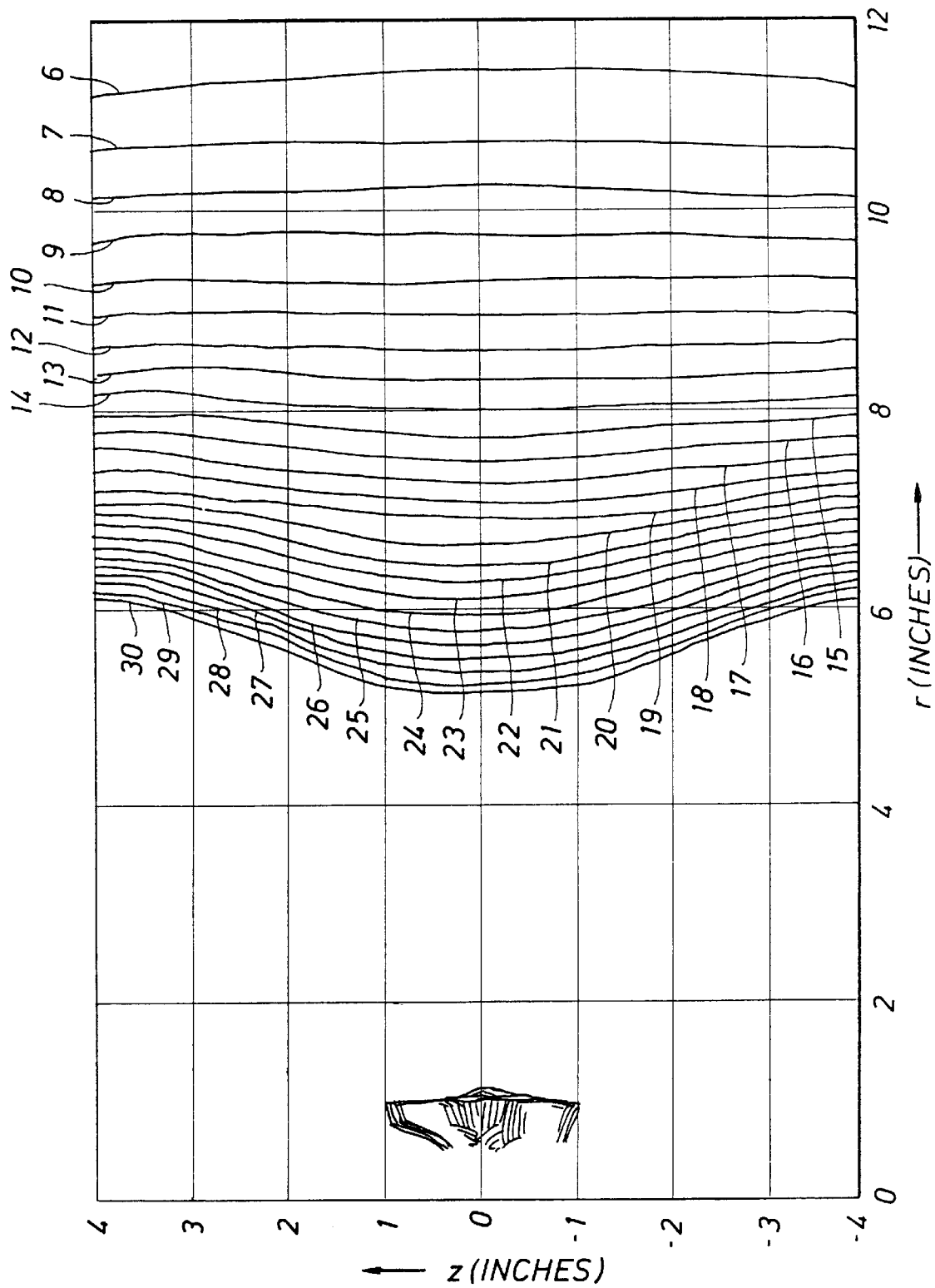
FIG. 4b represents the contour lines of the gradient $|\Delta B_0|$ corresponding to the high gradient magnet configuration.

The high gradient sonde is improved by inserting a magnetically permeable member 16 between magnets 30, 34. FIG. 4a represents contour lines of $|\vec{B}_0|$ corresponding to a configuration where magnetically permeable member 16 separates the upper 34 and central 30 magnets by eight inches. The contour lines of FIG. 4a show a slightly stronger field indicating a better signal-to-noise ratio and less curvature in the axial direction than the contour lines of FIG. 2c. Also, as illustrated in FIG. 4b, the magnetically permeable member 16 produces a more constant gradient $|\Delta B_0|$ in the axial direction that may simplify interpretation of the NMR measurements influenced by diffusion.

In the case of the high gradient sonde, as with other gradient designs, the proton rich borehole region surrounding the tool 10 will resonate only at frequencies higher than those being applied to the volume of investigation, i.e., there is no proton borehole signal. The high gradient sonde is sensitive to a small part of the sodium from the borehole fluid. For a 30% NaCl concentration borehole fluid, possibly the worst case, the error of the estimated porosity due to the sodium signal is approximately 0.08 pu. In the low gradient sonde, the sodium signal is substantially smaller than in the high gradient sonde. Consequently, the sodium signal is negligible for both NMR sondes.

Antennas and Gradient Coils

Referring to FIGS. 2 and 4, an RF magnetic field is created in the regions of investigation by antennas 36, 38 which are provided in recessed areas 50, 52. The RF field may be produced by one or more RF antenna segments that transmit and/or receive from different circumferential sectors of the logging device. See U.S. patent application Ser. Nos. 08/880,343 and 09/094,201 assigned to Schlumberger Technology Corporation. Preferably, each antenna 36, 38 comprises a coil 18 wound circumferentially around the recessed area 50, 52. The RF field created by such a coil arrangement is substantially axisymmetric. It is within contemplation of the subject invention to utilize the antenna 36, 38 for detecting NMR signals. However, a separate antenna or receiver may be used to detect the signals. A non-conductive material 54 is provided in the recessed area 50, 52 beneath the antenna 36, 38. The material 54 is preferably a ferrite to increase the efficiency of the antenna 36, 38. Alternatively, the material 54 may comprise plastic, rubber, or a reinforced epoxy composite material. The antennas 36, 38 are resonated by RF circuitry to create an RF magnetic field in the regions of investigation.

The recessed area 52 forms a shallow groove in the drill collar without reducing the inner diameter of the drill collar, which is ordinarily done to increase strength in a region of drill collar where the outer diameter has been recessed to provide an antenna. The recessed area 50 has a greater depth than recessed area 52. Due to mechanical constraints, it is only possible to have one deeply recessed area where the drill collar inner diameter is substantially reduced. It is within contemplation of the subject invention for the recessed areas 50, 52 to have substantially the same depth or for recessed area 52 to have a greater depth than area 50.

The cylindrical shells of spins in the region of investigation can be segmented axially or, preferably, azimuthally by using at least one directionally sensitive gradient coil 56 arranged in the recessed area 50 and/or 52. In a preferred embodiment of the invention, three gradient coils are positioned circumferentially around the recessed area and separated by an angular distance segment of 120°. Other quantities of gradient coils may be defined, either lesser or greater in number than three, and such coils may be separated by angular distances other than 120° and/or unequal angular segments. Each coil 56 is constructed with loops of wire, which conform to the curvature of the outer surface of the material 54. The magnetic field produced by each gradient coil 56 in a region of the formation facing the coil is substantially parallel to the static magnetic field produced by the magnets.

As is known to those skilled in the art, in the basic NMR measurement, a pulse sequence is applied to the formation under investigation. In U.S. Pat. No. 5,596,274 issued to Abdurrahman Sezginer and U.S. Pat. No. 5,023,551 issued to Kleinberg et al., a pulse sequence, such as the Carr-Purcell-Meiboom-Gill (CPMG) sequence, first applies an excitation pulse, a 90° pulse, to the formation that rotates the spins into the transverse plane. After the spins are rotated by 90° and start to dephase, the carrier of the refocusing pulses, the 180° pulses, is phase shifted relative to the carrier of the 90° pulse sequence according to the following relationship:

$t_{90°_{\pm x}} - t_0 - [t_{180°_y} - t_1 - \text{echo}_{max}{}^n - t_2]_n,$ where the bracketed expression is repeated for n=1,2, ... N, where N is the number of echoes collected in a single CPMG sequence and the echo spacing is $t_{echo} = 2t_{cp} = t_{180°_y} + t_1 + t_2$. $90°_{\pm x}$ denotes an RF pulse that causes the spins to rotate by a 90° angle about the $\pm$x-axis, as commonly defined in the rotating frame of magnetic resonance measurements (phase alternated). The time between application of the 90° pulse and the 180° pulse, $t_0$, is less than $t_{cp}$, half the echo spacing. The CPMG sequence enables acquisition of a symmetric measurement (i.e., a measurement without using the gradient coils). The exact timing parameters, $t_0$, $t_1$, and $t_2$, depend on various factors (e.g., the shape of the applied pulses).

In the subject invention, a current pulse applied to gradient coil 56 generates an additional magnetic field, substantially parallel to the static magnetic field. The current pulse is applied between the first 90° and the 180° phase reversing pulse. This additional field causes an additional phase shift for the spins. Since the 180° phase reversing pulse does not compensate for the additional phase shift, the spins subjected to the additional field do not form a spin-echo. However, for spins not subjected to the additional field, a spin-echo occurs at time $2t_{cp}$ with spin-echoes of successively lower amplitude occurring at time $t_{cp}$ after each phase reversing pulse. The pulse sequence is $t_{90°_{\pm x}} - t_0{}^a - \delta - t_0{}^b - [t_{180°_y} - t_1 - \text{echo}_{max}{}^n - t_2]_n$, where $t_0{}^a$ is the time between the 90° pulse and the gradient pulse of duration $\delta$, $t_0{}^b$ is the time between the gradient pulse and the 180° reversing pulse, and $t_0{}^a + \delta + t_0{}^b = t_0$. Due to the succeeding $180°_y$ pulses and the inhomogeneous fields, the x-component of the NMR signal will decay within a few echoes. Therefore, we focus only on the y-component of the signal. Thus, neglecting relaxation, the first NMR echo signal can be represented as:

$$\text{Signal} = \Im m [\int_{r \in R} {}^3 (M_x{}^0 + iM_y{}^0)(r) \exp(-i\gamma G(r)\delta) dc(r)],$$

where i is the imaginary complex unit; $\gamma$ is the gyromagnetic ratio; $M_x{}^0$ and $M_y{}^0$ are respectively x and y components of the magnetization at location r at the time of the first echo in the absence of the gradient pulse; G(r) is the component of the gradient field parallel to $\vec{B}_0$ at the same location; $\delta$ is the duration of the gradient pulse; and dc(r) denotes the differential sensitivity of the NMR sonde.

The gradient coils 56 offer a number of advantages for obtaining azimuthal measurements. First, because the axisymmetric antenna detects the spin-echoes, long echo trains can be recorded while the tool rotates in the borehole. Second, the coil 56 simplifies the design of an NMR-LWD tool because the coil 56 does not have the tuning requirements of an RF antenna 36, 38. Third, the same antenna 36, 38 can be used to make symmetric and axisymmetric measurements. Fourth, the coils 56 can be used to obtain NMR measurements with excellent spatial resolution, particularly vertical resolution.

Different modes for obtaining azimuthal NMR measurements are contemplated by the present invention. For example, a "simple spoiling" mode uses at least one coil 56 to spoil the spins in a selected quadrant where a quadrant is defined as an angular distance segment about the periphery of the tool 10, however, more coils 56 may be used to spoil a plurality of quadrants. In either case, two measurements are obtained: a symmetric phase alternated pulse sequence (PAPS) with a fixed wait time followed by a gradient PAPS having a variable wait time, with the selected quadrant spoiled by firing the coil 56 in the quadrant. In a preferred embodiment of the invention, the aforementioned gradient pulse sequence is used. Subtracting the gradient measurement from the symmetric measurement creates the azimuthal measurement. In this mode, one symmetric measurement is obtained for every two PAPS and one azimuthal scan is obtained for every eight PAPS. The measurement noise for the azimuthal measurement is higher than the noise in the symmetric or gradient measurement because the two measurements are combined.

It is possible to reduce the noise contribution by combining different single quadrant spoiling measurements. For example, four gradient PAPS measurements may be obtained by spoiling each quadrant. The measurements are combined to create a synthetic azimuthal and symmetric measurement. By combining measurements made without the gradient coils 56 being fired with measurements made with one or more gradient coils 56 being fired, axially or azimuthally resolved "images" of the formation can be generated. The acquired data, particularly in the form of azimuthal images of porosity and bound fluid, are very desirable for improved petrophysical interpretation in highly deviated and horizontal wellbores and for decision-making while drilling for geologically based wellbore placement.

Optimizing the Pulse Length and Operating Frequency

For a chosen operating RF frequency, there is an optimum duration for the 90° pulse, $t_{90}$, as well as for the 180° pulses, $t_{180}$, which ensures a desired signal-to-noise ratio. The search for an optimal pulse length may be performed during the master calibration of the tool, so that all pulse lengths will be correctly initialized, or when the static magnetic field changes in an unpredictable manner, such as a change due to accumulation of magnetic debris during the drilling process. See U.S. patent application Ser. No. 09/031,926 assigned to Schlumberger Technology Corporation. This technique may also be used to choose the appropriate frequency to meet other criteria, such as keeping the depth of investigation constant.

The optimal pulse length may be determined by measuring the NMR response of a sample using at least two different pulse durations and using a predefined mode independent of the NMR properties of the formation. Alternatively, the optimal pulse length may be determined using at least two different pulse durations and additionally using a mode computed from the NMR properties of the formation. In the first case, stacking the data improves the signal-to-noise ratio, however, the stacking procedure may require a long period of time to acquire data from the formation. Preferably, the measured data are accumulated during a stationary time window when the tool 10 pauses from the drilling operation, such as during the time when a new section of drill pipe is added to the drill string. In the second case, if the $T_2$ distribution of the formation is known, a best acquisition mode may be constructed which provides the largest signal-to-noise ratio for a unit of acquisition time and provides an optimal linear combination of the acquired echoes. Laboratory simulations show that optimum timing for the best acquisition mode is achieved when the duration of the echo train is approximately equal to $T_{2,\,max}$, the dominate $T_2$ of the formation, and when the wait time, $t_w$, is approximately equal to $2.5 \times T_{2,max}$ (assuming a constant $T_1/T_2$ ratio of 1.5). The best acquisition mode determines the optimal pulse length to within a few percent over several seconds. A similar technique may be used to optimize the NMR signal with respect to the frequency (e.g., saddle point design). The $T_2$ distribution effectively aids the efficient tuning of pulse lengths for the tool 10.

Data Acquisition Modes

As described above, tool 10 has a plurality of antennas 36, 38. In a preferred embodiment of the invention, these antennas 36, 38 do not transmit or acquire data simultaneously. Preferably, after one antenna 36 acquires data, the other antenna 38 experiences a minimum wait time while the power supply recharges in order to transmit the next pulse sequence. It is within contemplation of the subject invention to transmit or acquire data simultaneously. Further, this invention contemplates data acquisition without a requisite wait time.

Based on these design preferences, a plurality of data acquisition modes may be used. By way of example, three representative timings for NMR data acquisition are described below: a fast timing suitable for water-wet sandstone zones, a slow timing appropriate for carbonate zones, and a very slow timing designed for hydrocarbon bearing zones (or invasion of oil based mud). The timings are set forth in Table I.

TABLE I

|  | Wait Time (sec.) | Echo spacing (msec) | Number of Echoes |
| --- | --- | --- | --- |
| Fast | 2.3 | 0.5 | 400 |
| Slow | 4.6 | 0.5 | 800 |
| very slow | 9.2 | 1.0 | 800 |

Figure 5A:
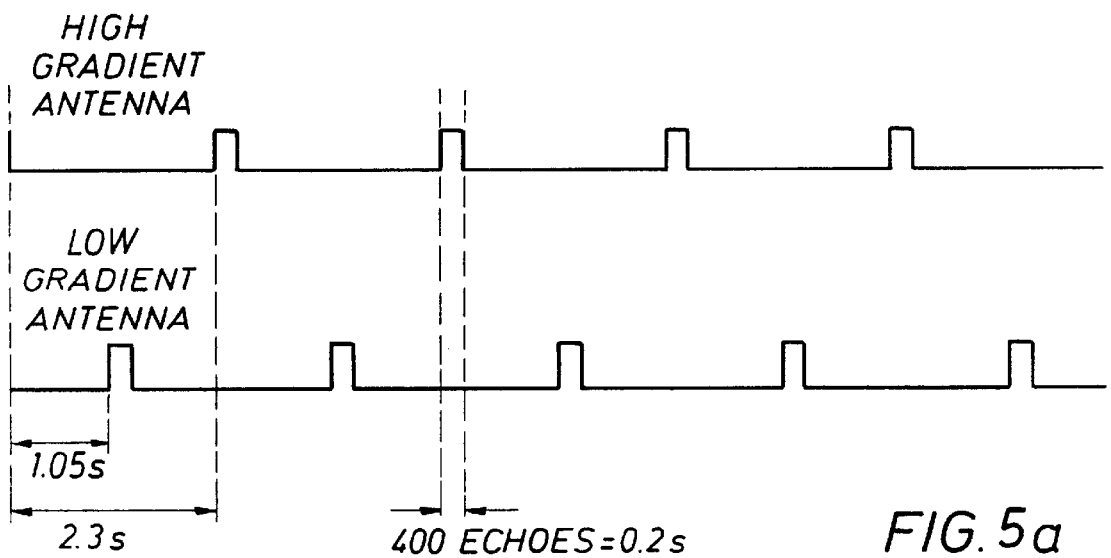
FIG. 5 depicts the simple data acquisition mode.
Figure 5B:
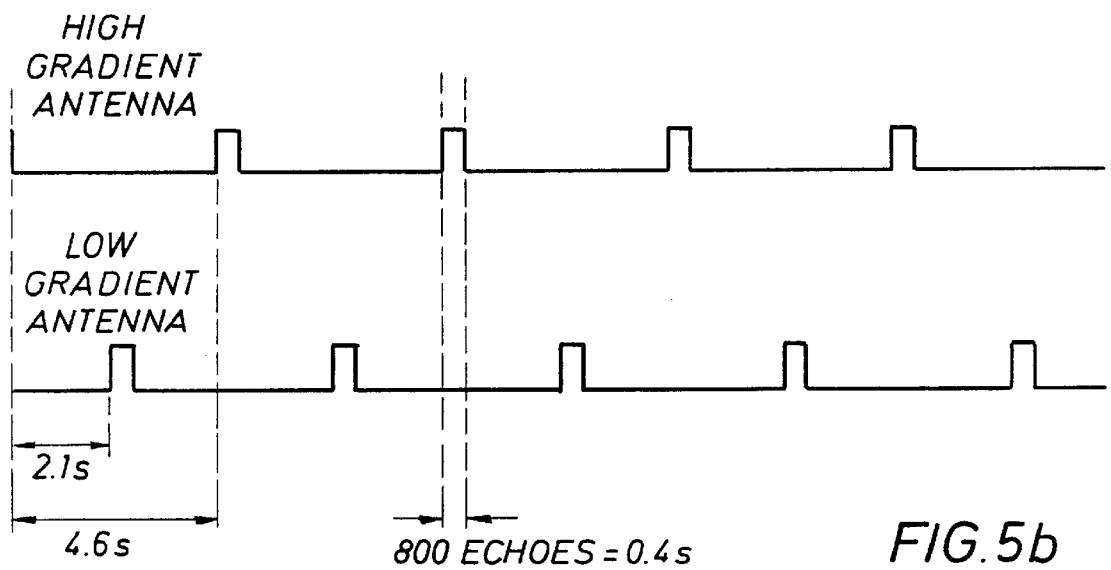
Figure 5C:
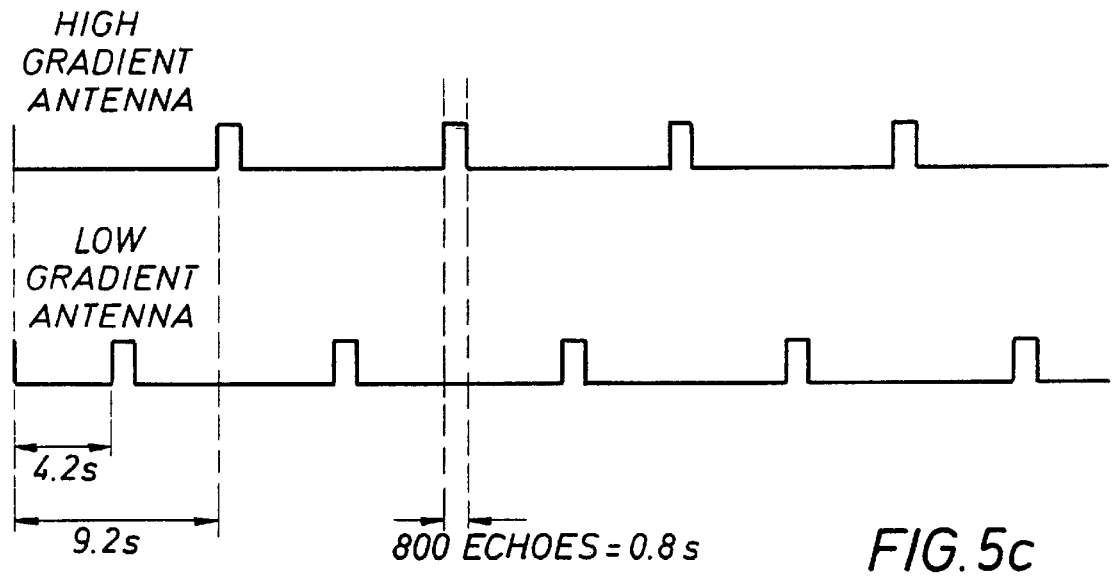

Several different modes may be used with each data acquisition timing, including, but not limited to, the following: simple, interleaved, and bursts. The simplest way to acquire $T_2$ information with the tool 10 is to perform CPMG measurements with both antennas 36, 38 using the same timing. FIG. 5 illustrates the simple data acquisition mode used with the fast decaying, slowly decaying, and very slowly decaying timing from Table I. Each antenna 36, 38 alternately acquires a long pulse sequence which provides an effective porosity measurement from each antenna 36, 38.

Figure 6A:
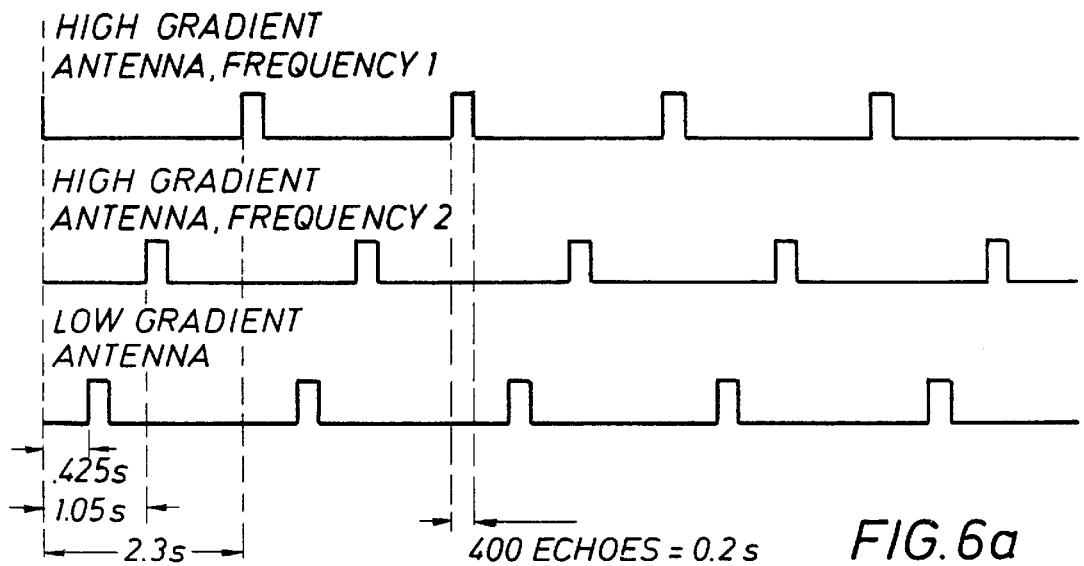
FIG. 6 depicts the interleaved data acquisition mode.
Figure 6B:
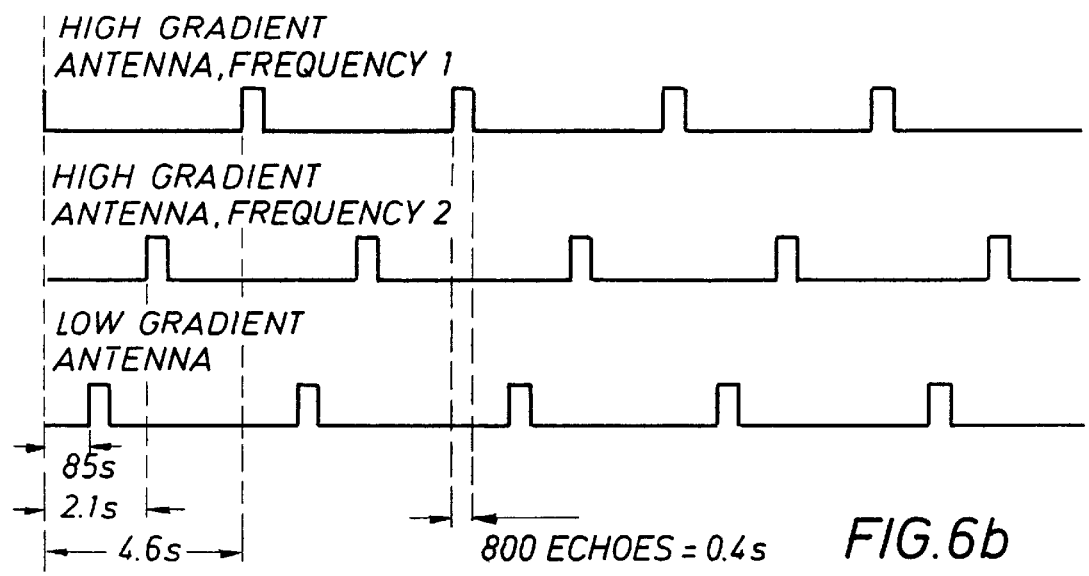
Figure 6C:
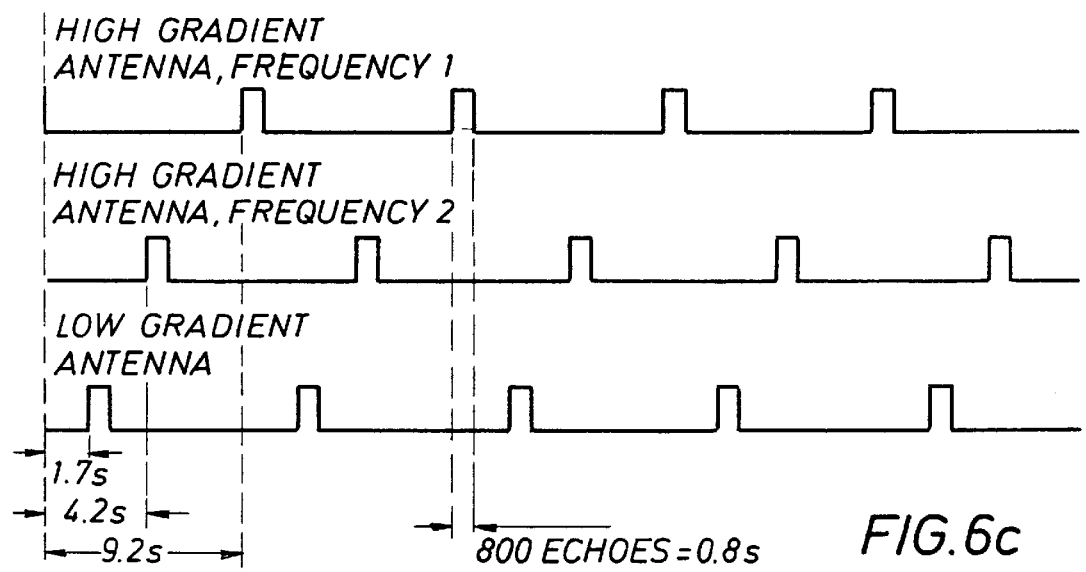

With the interleaved mode, the high gradient antenna measures at least two cylindrical shells at two different frequencies while the low gradient antenna obtains a measurement using a single frequency. FIG. 6 illustrates an interleaved measurement for fast decaying samples, slowly decaying components, and very slowly decaying components using the timing from Table I.

Figure 7A:
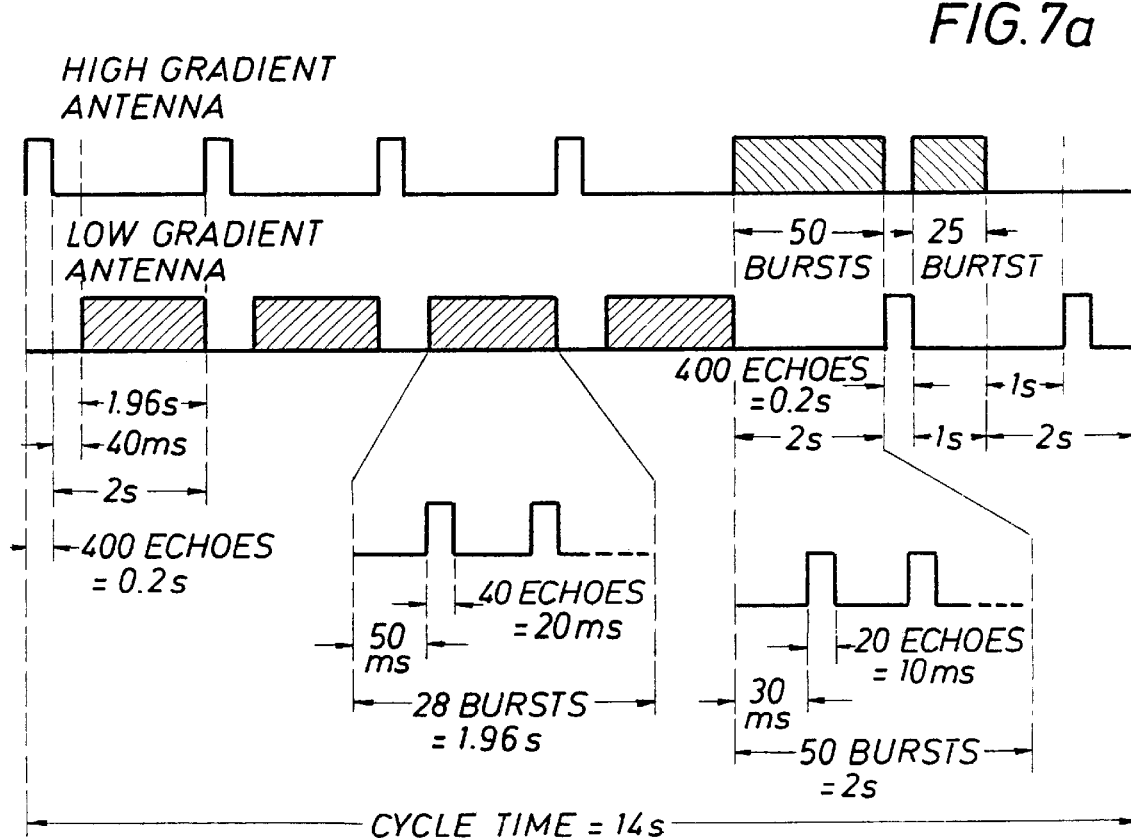
FIG. 7 depicts the burst data acquisition mode.
Figure 7B:
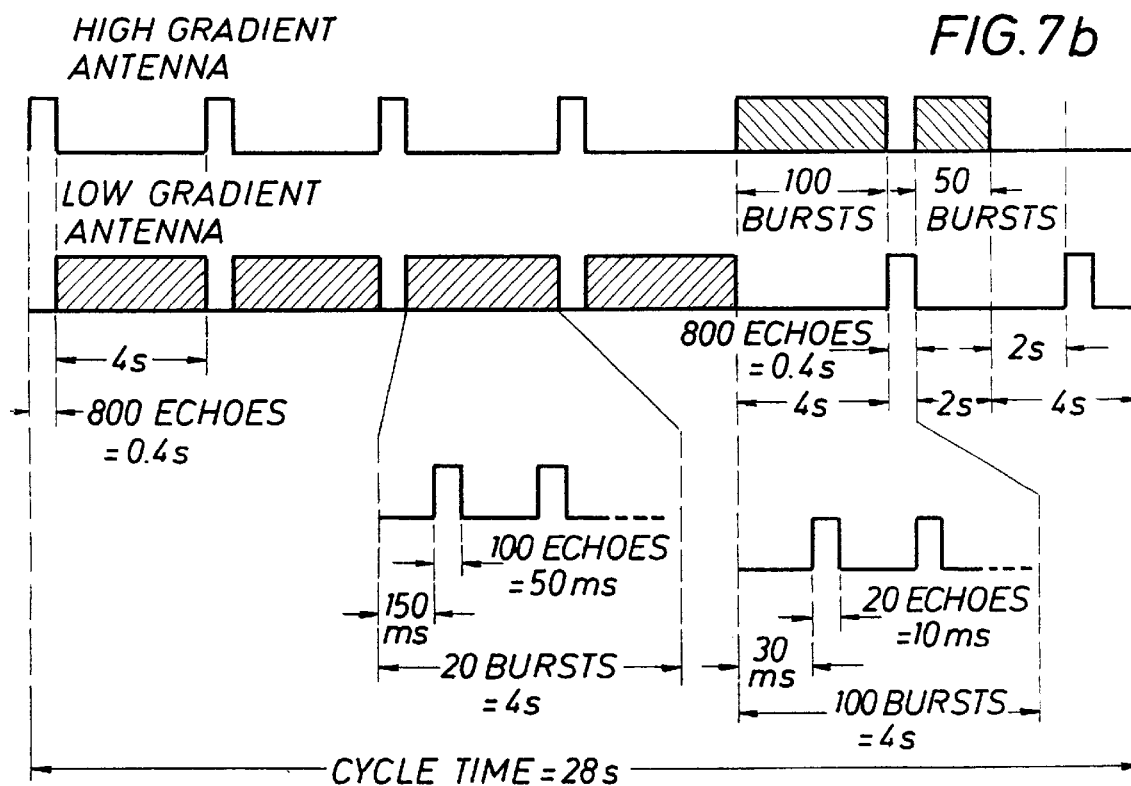
Figure 7C:
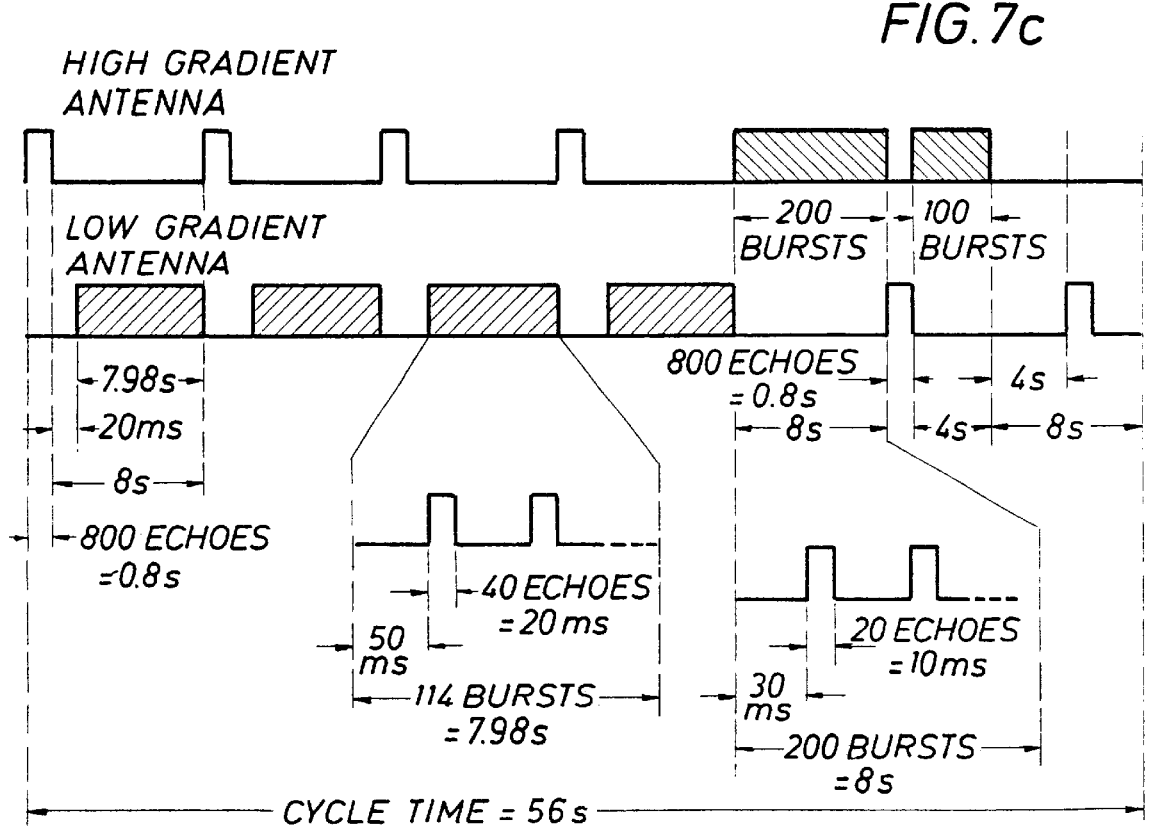

The burst mode enhances the signal-to-noise ratio, especially for the fast decaying components. In addition, the burst mode provides a useful $T_1$ based bound fluid measurement. See WO 98/29639 assigned to Numar Corporation [describes a method for determining longitudinal relaxation times, $T_1$]. Also, see U.S. patent application Ser. No. 09/096, 320 assigned to Schlumberger Technology Corporation [describes a method for polarizing the bound fluid of a formation]. FIG. 7 illustrates burst measurements for fast decaying samples, slowly decaying components, and very slowly decaying components using slightly modified times from Table I.

In addition to the simple, interleaved, and burst modes, with the subject invention, it is possible to optimize formation evaluation measurements by detecting downhole conditions which create a pause during the drilling operation, determining the drilling mode, and using the mode to control data acquisition. Standard rotary drilling operations contain many natural pauses where the tool remains stationary: connection time as a new section of drill pipe is added to the drill string, circulation time when mud is circulated and the drill pipe is possibly rotated, and fishing or jarring time while the drill string is stuck and has to be freed before drilling can resume. These natural pauses, which occur without interrupting normal drilling operations, or deliberately initiated pauses, are utilized to make NMR measurements. The drilling modes include, but are not limited to, drilling, sliding, tripping, circulating, fishing, a short trip (up or down), and drill pipe connections. Determining the drilling mode enhances the ability to obtain NMR measurements that take a long time or that benefit from a quiet environment, e.g., $T_1$, $T_2$, antenna tuning, and hydrocarbon typing. See U.S. patent application Ser. No. 09/031,926 assigned to Schlumberger Technology Corporation. It is also possible to adjust acquisition modes based on changes in the environment (e.g., washout, salinity, etc.) and/or changes in the formation NMR properties (e.g., long $T_1$ versus short $T_1$).

The spin-echo amplitudes are obtained by hardware integration of the receiver voltages over a time window. The tool 10 uses phase sensitive detection to measure the in-phase and quadrature components of the spin-echo signal-plus-noise amplitudes. The techniques disclosed in U.S. Pat. No. 5,381,092 issued to Robert Freedman may be used to compute window sums downhole and transmit the window sums to the surface for $T_2$ inversion processing and presentation. Also, the techniques disclosed in U.S. Pat. No. 5,363,041 issued to Abdurrahman Sezginer may be implemented to utilize a linear operator to map a relaxation-time distribution to spin-echoes, produce a singular value decomposition (SVD) of the linear operator, determine vectors of the SVD, and compress the spin-echo data using the vectors. Preferably, the $T_2$ spectrum is computed downhole and transmitted to the surface. This offers the advantage of eliminating a telemetry bottleneck created by transmitting the data required to compute the $T_2$ spectrum to the surface. A digital signal processor may be used to invert the $T_2$ data. The amplitudes, $A_j$, of the spin-echoes are characterized by the following relationship:

$$A_j = \sum_{i=1}^{M} X_{ji} a_i + \eta_j,$$

where $\eta_j$ is the noise in the measurement $A_j$, $a_i$ is the amplitude of the $T_2$ distribution taken at $$X_{ji} = \exp\left(-\frac{j\Delta t}{T_{2i}}\right)\left(1 - \exp\left(-\frac{t_w}{cT_{2i}}\right)\right)$$

represents the elements of matrix x, where $t_w$ is the wait time and c is a constant (the $T_1/T_2$ ratio), $\Delta t$ is the echo spacing, and j=1,2, ... N, where N is the number of echoes collected in a single pulse sequence. In matrix notation, the equation becomes $\vec{A} = X\vec{a} + \vec{\eta}$. Since the noise, $\eta$, is unknown, $\vec{a}$ can be approximated by finding a least squares solution, i.e., a minimum of the functional $J = \|\vec{A} - X\vec{a}\|^2$. The solution of this equation is strongly affected by noise present in the data and the solution may have negative components even though the $T_2$ spectrum does not have negative components. To overcome this problem, a regularization term, $\lambda \|\vec{a}\|^2$, is added to the functional and the functional $J_\lambda(\vec{a}) = \|\vec{A} - X\vec{a}\|^2 + \lambda \|\vec{a}\|^2$ is minimized using a suitable iterative minimization algorithm (e.g., Conjugated Gradient Projection Method) under the constraint that $a_i \geq 0$ for i=1. . . M. See Ron S. Dembo and Ulrich Tulowitzski, *On the Minimization of Quadratic Functions Subject to Box Constraints*, Yale Department of Computer Science (September 1984) (describes the Conjugated Gradient Projection Method). The necessary time for performing the $T_2$ inversion using a digital signal processor is very reasonable. For example, assuming 1800 echoes and 30 samples in the $T_2$ domain, the inversion on a digital signal processor requires less than two seconds.

Pulse Programmer

Figure 8:
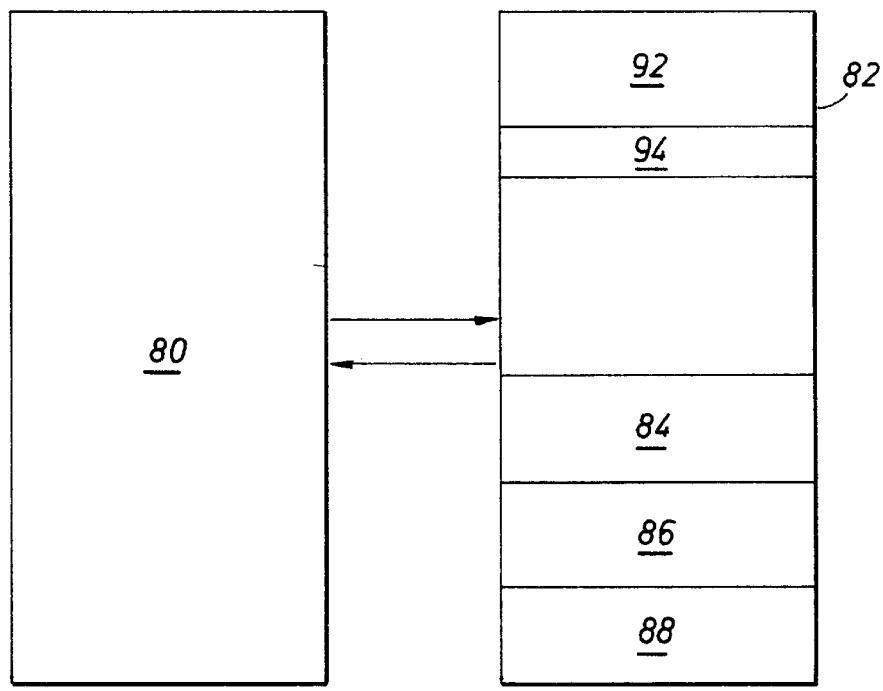
FIG. 8 represents a block diagram of the pulse programmer.

For the basic NMR measurement with tool 10, electronic circuitry applies a pulse sequence to the formation under investigation. Tool 10 includes a pulse programmer 80, which adaptively selects and controls the pulse sequences applied to the formation. The pulse programmer 80 establishes the pulse sequence using information found in the Measurement Control Block 82 (See FIG. 8) and the operating conditions of the tool 10. Preferably, the Measurement Control Block 82 is stored in a downhole memory device. The structure of block 82 is fixed to allow pulse programmer 80 easily to adapt and change the timing of the pulse sequences autonomously downhole. It is advantageous to partition a portion of block 82 into a plurality of tables 84, 86, and 88. Instead of controlling all tool operations that depend on the pulse sequence from the pulse programmer 80, the tables 84, 86, 88 are used to control these operations. This allows the pulse programmer 80 to vary the pulse sequences without introducing contradictions in the tool configuration. The plurality of tables 84, 86, and 88 may include, but are not limited to, the following: a buffer table which describes the layout of stacking buffers, an acquisition table which defines the acquired signals accumulated in buffers, a filter coefficient table which prescribes the detection filter employed with a signal acquisition, a spin dynamics correction table which designates the spin dynamics correction to be used for each buffer, and a data processing table which designates the nuclear magnetic resonance characteristic calculated from the acquired buffers.

The pulse programmer 80 includes a pulse sequence template 94, useful for generating pulse sequences, which comprises a sequence of states dependent on repetition and timing variables. These variables are calculated from sequence configuration parameters using the calculation block 92. The calculation block 92 may be implemented as an executable or interpretive structure. Based on the physical quantity that will be measured, e.g. $T_2$, timing variables may be defined such as the wait time, $t_w$, the echo spacing, $t_{echo}$, and the number of acquired echoes. The configuration parameters include, but are not limited to, $t_{90}$, pulse amplitude, and pulse shape. These parameters may be calculated periodically during calibration of the tool 10 or during operation of the tool 10 since those parameters may vary as the operating conditions of the tool 10 vary. For example, the pulse amplitude and shape depends on the antenna quality factor and, therefore, on the conductivity of the formation surrounding the tool 10.

Normally, after pulse programmer 80 initiates a pulse sequence, the sequence runs deterministically until it is finished. To implement certain azimuthal measurement modes with tool 10, the pulse programmer 80 has the ability to vary the pulse sequence during execution of the sequence. Programmer 80 may stop execution of the pulse sequence and enter a HALT state until an external signal ends the state at time $t_c$ or until a maximum time period, $t_{max}$, has expired. As previously discussed in the Data Acquisition Modes section of this specification, since at least one of the different modes (interleaved) which may be used with the data acquisition timing contemplates interleaving several measurements, the programmer 80 compensates for the time that passed during the HALT state. Preferably, compensation is accomplished by grouping HALT events. For example, a grouping may comprise a pair of HALT events where one HALT event operates as previously described and the other HALT event is a normal event of duration $t_{max}-t_c$. Grouping events allows the programmer 80 to combine sequences having variable and deterministic timing.

In addition, the sequence of states, as defined in the pulse sequence template 94, may comprise several alternatives for parts of the sequence. In real time, one of the alternatives (branching) is chosen dependent on external conditions of the tool (e.g., the azimuth of the tool).

The foregoing description of the preferred and alternate embodiments of the present invention has been presented for purposes of illustration and description. It is not intended to be exhaustive nor to limit the invention to the precise form disclosed. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What we claim is:

1. An apparatus for determining a nuclear magnetic resonance property in an investigation region of earth formations surrounding a borehole, comprising:
    a) a drilling means for drilling a borehole into the formation;
    b) a means for carrying drilling fluid through the drilling means;
    c) a measuring means, connected to the drilling means, for making nuclear magnetic resonance measurements while the borehole is being drilled, the measuring means comprising:
        i) means for producing a plurality of substantially axisymmetric static magnetic fields through the drilling means and into the formation at a plurality of regions of investigation where the nuclear magnetic resonance measurement is obtained such that contour lines generated by at least one static magnetic field are substantially straight in the axial direction; and,
        ii) means for producing an oscillating magnetic field in the formation;
    a) at least one magnetically permeable member located inside the drilling means for shaping the static magnetic field;
    b) gradient means in the logging device for applying a magnetic field gradient to dephase spins in a portion of the investigation regions; and,
    c) means for detecting nuclear magnetic resonance signals from the investigation regions.

2. The apparatus of claim 1 wherein the means for producing a plurality of axisymmetric static magnetic fields further comprises means for producing at least one static magnetic field having a low gradient in at least one region of investigation.

3. The apparatus of claim 1 wherein the means for producing a plurality of axisymmetric static magnetic fields further comprises means for producing at least one static magnetic field having a high gradient in at least one region of investigation.

4. The apparatus of claim 1 wherein the means for producing a plurality of axisymmetric static magnetic fields further comprises means for producing at least one static magnetic field having a high gradient in a first region of investigation and means for producing at least one static magnetic field having a low gradient in a second region of investigation.

5. The apparatus of claim 1 wherein the means for producing the oscillating magnetic field in the formation further comprises means for producing a plurality of oscillating magnetic fields in the formation.

6. The apparatus of claim 4 wherein the means for producing the oscillating magnetic field in the formation further comprises means for producing a plurality of oscillating magnetic fields in the formation.

7. The apparatus of claim 6 wherein the means for producing a plurality of oscillating magnetic fields further comprises a first antenna for producing at least one oscillating magnetic field in at least one region of investigation.

8. The apparatus of claim 7 wherein the means for producing a plurality of oscillating magnetic fields further comprises a second antenna for producing at least one oscillating magnetic field in at least one region of investigation.

9. The apparatus of claim 7 wherein the drilling means further comprises a tubular drill collar having a generally cylindrical inner surface having an inner diameter and a generally cylindrical outer surface having an outer diameter wherein the first antenna is disposed in a first recess spanning an axial extent in the outer surface, the outer surface having a diameter that is reduced from the outer diameter over the axial extent of the first recess, and the inner surface of the drill collar having a diameter that is not substantially reduced from the inner diameter over the axial extent of the first recess.

10. The apparatus of claim 8 wherein the second antenna is disposed in a second recess spanning an axial extent in an outer surface of the drilling means, the outer surface having a diameter that is reduced from the outer diameter of the drilling means over the axial extent of the second recess.

11. The apparatus of claim 8 wherein the drilling means further comprises a tubular drill collar having a generally cylindrical inner surface having an inner diameter and a generally cylindrical outer surface having an outer diameter wherein the second antenna is disposed in a second recess spanning an axial extent in the outer surface, the inner surface of the drill collar having a diameter that is not substantially reduced from the inner diameter over the axial extent of the second recess.

12. The apparatus of claim 8 wherein the drilling means further comprises a tubular drill collar having a generally cylindrical inner surface having an inner diameter and a generally cylindrical outer surface having an outer diameter wherein the second antenna is disposed in a second recess spanning an axial extent in the outer surface, the inner surface of the drill collar having a diameter that is substantially reduced from the inner diameter over the axial extent of the second recess.

13. The apparatus of claim 9 wherein the first antenna produces the at least one oscillating magnetic field in the first region of investigation.

14. The apparatus of claim 10 wherein the second antenna produces the at least one oscillating magnetic field in the second region of investigation.

15. The apparatus of claim 1 wherein the gradient means further comprises a plurality of gradient means positioned around the circumference of the drilling means.

16. The apparatus of claim 1 wherein the means for carrying drilling fluid through the drilling means further comprises a magnetically permeable member having a plurality of recessed areas.

17. The apparatus of claim 16 further comprising means for covering the recessed areas.

18. A method for determining a nuclear magnetic resonance property in an investigation region of earth formations surrounding a borehole, comprising the steps of:
   a) providing a device that is moveable through the borehole;
   b) generating, from the device, a plurality of substantially axisymmetric static magnetic fields into the formation at a plurality of regions of investigation;
   c) generating, from the device, an oscillating magnetic field into the formation;
   d) shaping at least one static magnetic field such that contour lines generated by the field are substantially straight in the axial direction; and,
   e) detecting nuclear magnetic resonance signals from the regions of investigation.

19. The method of claim 18 wherein step (a) further comprises the step of producing at least one static magnetic field having a low gradient in at least one region of investigation.

20. The method of claim 18 wherein step (a) further comprises the step of producing at least one static magnetic field having a high gradient in at least one region of investigation.

21. The method of claim 18 wherein step (a) further comprises the step of producing at least one static magnetic field having a saddle point in at least one region of investigation.

22. The method of claim 18 wherein step (a) further comprises the steps of: producing at least one static magnetic field having a high gradient in a first region of investigation and producing at least one static magnetic field having a low gradient in a second region of investigation.

23. The method of claim 22 wherein step (b) further comprises the step of producing a plurality of oscillating magnetic fields in the formation.

24. The method of claim 22 further comprising the steps of producing an oscillating magnetic field in the first region of investigation and producing an oscillating magnetic field in the second region of investigation.

25. The method of claim 18 further comprising the step of applying a magnetic field gradient to dephase spins in a portion of at least one region of investigation.

26. The method of claim 25 further comprising the step of partitioning a cross-section of the formation into a plurality of angular distance segments around the borehole and spatially varying the strength of at least one static magnetic field in at least one segment so that a net magnetization over the segment is substantially zero.

27. The method of claim 25 further comprising the step of partitioning a cross-section of the formation into a plurality of angular distance segments around the borehole and spatially varying the strength of at least one static magnetic field in at least one segment so that a net magnetization over the segment is non-zero and has a different phase than the net magnetization in the remaining portion of the investigation.

28. The method of claim 25 further comprising the step of partitioning a cross-section of the formation into a plurality of axial segments and spatially varying the strength of at least one static magnetic field in at least one axial segment so that a net magnetization over the segment is substantially zero.

29. The method of claim 25 further comprising the step of partitioning a cross-section of the formation into a plurality of axial segments and spatially varying the strength of at least one static magnetic field in at least one axial segment so that a net magnetization over the segment is non-zero and has a different phase than the net magnetization in the remaining portion of the investigation.

30. The method of claim 24 further comprising the step of alternately generating a sequence of pulses and spin-echoes in the first and second region of investigation.

31. The method of claim 18 further comprising the steps of applying a sequence of magnetic field pulses to the formation and determining an optimal length of time each pulse is applied to the formation.

32. The method of claim 31 wherein the step of determining an optimal length of time each pulse is applied to the formation further comprises the steps of selecting at least two different lengths of time, applying the sequence of pulses using the at least two different lengths of time, and detecting nuclear magnetic resonance signals from the regions of investigation.

33. The method of claim 31 further comprising the steps of drilling the borehole into the formation using the device; while drilling the borehole, detecting a pause where a portion of the device remains stationary with respect to the formation for a time interval; and determining the optimal length of time during the time interval.

34. The method of claim 31 wherein the step of determining an optimal length of time each pulse is applied to the formation further comprises utilizing a $T_2$ distribution of the formation to determine the optimal length.

35. The method of claim 31 further comprising the step of optimizing an operating frequency.

36. The method of claim 18 further comprising the step of sequentially detecting nuclear magnetic resonance signals from each region of investigation.

37. The method of claim 18 further comprising the step of simultaneously detecting nuclear magnetic resonance signals from each region of investigation.

38. The method of claim 36 further comprising the steps of detecting nuclear magnetic resonance signals from a first region of investigation; waiting a period of time; and detecting nuclear magnetic resonance signals from a second region of investigation.

39. The method of claim 18 further comprising the step of sequentially producing a plurality of oscillating magnetic fields into the formation.

40. The method of claim 18 further comprising the step of simultaneously producing a plurality of oscillating magnetic fields into the formation.

41. The method of claim 18 further comprising the steps of detecting nuclear magnetic resonance signals from a first region of investigation and simultaneously producing an oscillating magnetic field into the second region of investigation.

42. The method of claim 18 further comprising the steps of detecting nuclear magnetic resonance signals from a first region of investigation; waiting a period of time; and producing an oscillating magnetic field into the second region of investigation.

43. The method of claim 22 further comprising the steps of producing at least one oscillating magnetic field in the first region of investigation and producing at least one oscillating magnetic field in the second region of investigation.

44. The method of claim 43 further comprising the steps of applying a plurality of RF pulses having a frequency, $f_1$, in the first region of investigation; applying a plurality of RF pulses having a different frequency, $f_2$, in the first region of investigation; and applying a plurality of RF pulses in the second region of investigation.

45. The method of claim 43 further comprising the steps of applying a first plurality of RF pulses in the first region of investigation; and, during a wait time, applying a second plurality of RF pulses in the second region of investigation.

46. The method of claim 43 further comprising the steps of applying a first plurality of RF pulses in the second region of investigation; and, during a wait time, applying a second plurality of RF pulses in the first region of investigation.

47. The method of claim 18 further comprising the step of integrating information obtained from at least one device with the detected nuclear magnetic resonance signals in order to quality control the signals.

48. The method of claim 47 wherein the device comprises a strain gauge, an accelerometer, and/or a magnetometer.

49. The method of claim 18 further comprising the steps of drilling the borehole into the formation using the device; detecting nuclear magnetic resonance signals while drilling the borehole; and estimating device motion and compensating for the effect of the motion on the detected signals.

50. The method of claim 18 further comprising the step of controlling the quality of the detected signals.

51. The method of claim 18 further comprising the step of correcting the detected signals for the effect of device motion on the detected signals.

52. The apparatus of claim 1 wherein the means for producing a plurality of axisymmetric static magnetic fields further comprises means for producing at least one static magnetic field having a saddle point in at least one region of investigation.

* * * * *